United States Patent
Zhao et al.

(10) Patent No.: US 7,371,888 B2
(45) Date of Patent: May 13, 2008

(54) α-(TRIFLUOROMETHYL-SUBSTITUTED ARYLOXY, ARYLAMINO, ARYLTHIO OR ARYLMETHYL)-TRIFLUOROMETHYL-SUBSTITUTED PHENYLACETIC ACIDS AND DERIVATIVES AS ANTIDIABETIC AGENTS

(75) Inventors: Zuchun Zhao, Pleasanton, CA (US); Xin Chen, San Ramon, CA (US); Jianchao Wang, Castro Valley, CA (US); Hongbin Sun, Hayward, CA (US); Jack Shih-Chieh Liang, Mountain View, CA (US)

(73) Assignee: Metabolex, Inc., Hayward, CA (US)

( * ) Notice: Subject to any disclaimer, the term of this patent is extended or adjusted under 35 U.S.C. 154(b) by 168 days.

(21) Appl. No.: 11/061,302

(22) Filed: Feb. 17, 2005

(65) Prior Publication Data

US 2005/0222213 A1 Oct. 6, 2005

Related U.S. Application Data

(60) Provisional application No. 60/545,850, filed on Feb. 18, 2004.

(51) Int. Cl.
C07C 69/73 (2006.01)
C07C 315/00 (2006.01)
A01N 29/02 (2006.01)

(52) U.S. Cl. .............. 560/61; 514/746; 514/757; 562/430; 560/60

(58) Field of Classification Search ........... 514/746, 514/757; 560/60, 61; 562/430
See application file for complete search history.

(56) References Cited

U.S. PATENT DOCUMENTS

| 2,711,424 | A | 6/1955 | Suter et al. |
| 3,158,645 | A | 11/1964 | Newcomer et al. |
| 3,378,582 | A | 4/1968 | Bolhofer |
| 3,517,050 | A | 6/1970 | Bolhofer |
| 3,517,051 | A | 6/1970 | Bolhofer |
| 3,546,229 | A | 12/1970 | Griot |
| 3,564,042 | A | 2/1971 | Griot |
| 3,707,549 | A | 12/1972 | Mills |
| 3,816,446 | A | 6/1974 | Bolhofer |
| 3,860,628 | A | 1/1975 | Shuman |
| 3,923,855 | A | 12/1975 | Shuman |
| 3,953,490 | A | 4/1976 | Shuman |
| 4,067,996 | A | 1/1978 | Najer et al. |
| 4,072,754 | A | 2/1978 | Schacht et al. |
| 4,125,729 | A | 11/1978 | Trust et al. |
| 4,168,385 | A * | 9/1979 | Trust et al. ............ 560/56 |
| 5,041,640 | A | 8/1991 | Creger |
| 6,262,118 | B1 * | 7/2001 | Luskey et al. ............ 514/559 |

FOREIGN PATENT DOCUMENTS

| GB | 1403309 | 8/1975 |
| JP | 49051243 | 5/1974 |
| JP | 49051246 | 5/1974 |
| WO | WO 00/74666 | 12/2000 |
| WO | WO 03/080545 A2 | 12/2003 |

\* cited by examiner

*Primary Examiner*—Yvonne Eyler
*Assistant Examiner*—Yate' K Cutliff
(74) *Attorney, Agent, or Firm*—Townsend and Townsend and Crew LLP

(57) ABSTRACT

Compounds having a formula:

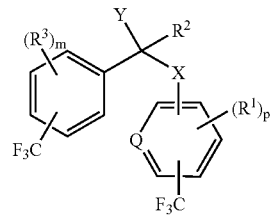

or a pharmaceutically acceptable salt or prodrug thereof, are provided, and are useful for the treatment of metabolic disorders.

10 Claims, No Drawings

α-(TRIFLUOROMETHYL-SUBSTITUTED ARYLOXY, ARYLAMINO, ARYLTHIO OR ARYLMETHYL)-TRIFLUOROMETHYL-SUBSTITUTED PHENYLACETIC ACIDS AND DERIVATIVES AS ANTIDIABETIC AGENTS

CROSS-REFERENCES TO RELATED APPLICATIONS

This application claims the benefit of U.S. Ser. No. 60/545,850, filed Feb. 18, 2004, the contents of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: Type 1 diabetes (formerly referred to as insulin-dependent diabetes or IDDM); and Type 2 diabetes (formerly referred to as non-insulin dependent diabetes or NIDDM).

Type 1 diabetes is the result of an absolute deficiency of insulin, the hormone which regulates glucose utilization. This insulin deficiency is usually characterized by β-cell destruction within the Islets of Langerhans in the pancreas, which usually leads to absolute insulin deficiency. Type 1 diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies.

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes, with hyperlipidemia being an important precipitating factor for these diseases.

Hyperlipidemia is a condition generally characterized by an abnormal increase in serum lipids in the bloodstream and, as noted above, is an important risk factor in developing atherosclerosis and heart disease. For a review of disorders of lipid metabolism, see, e.g., Wilson, J. et al., (ed.), *Disorders of Lipid Metabolism*, Chapter 23, Textbook of Endocrinology, 9th Edition, (W. B. Sanders Company, Philadelphia, Pa. U.S.A. 1998; this reference and all references cited therein are herein incorated by reference). Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. *Ann. Chim. Med.* (1927) 5: 1061-1079). Epidemiological studies since then have confirmed the association and have shown a several-fold increase in coronary deaths among diabetic subjects when compared with nondiabetic subjects (see, e.g., Garcia, M. J. et al., *Diabetes* (1974) 23: 105-11 (1974); and Laakso, M. and Lehto, S., *Diabetes Reviews* (1997) 5(4): 294-315). Several lipoprotein abnormalities have been described among diabetic subjects (Howard B., et al., *Artherosclerosis* (1978) 30: 153-162).

What is needed in the art are new compounds and methods useful for the treatment of insulin resistance, Type 2 diabetes, hyperlipidemia and hyperuricemia. The present invention fulfills this and other needs by providing such compounds, compositions and methods for alleviating insulin resistance, Type 2 diabetes, hyperlipidemia and hyperuricemia.

BRIEF SUMMARY OF THE INVENTION

In one aspect, the present invention provides compounds having a formula:

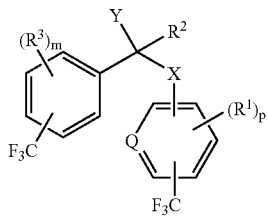

or a pharmaceutically acceptable salt or prodrug thereof, wherein the letter X represents a member selected from the group consisting of O, S, SO, SO$_2$, CHR and NR, wherein R is H, (C$_1$-C$_8$)alkyl, COR$^a$, COOR$^a$ and CONR$^a$R$^b$ wherein R$^a$ and R$^b$ are each independently selected from the group consisting of H and (C$_1$-C$_8$)alkyl; the letter Y represents a member selected from the group consisting of CH$_2$OR$^c$, CO$_2$R$^c$, tetrazole, CHO, CONR$^c$R$^m$, CH(=NR$^c$) and CH(=NOR$^c$), wherein R$^c$ is a member selected from the group consisting of H, (C$_1$-C$_8$)alkyl, (C$_3$-C$_8$)alkenyl, (C$_3$-C$_8$)alkynyl, (C$_3$-C$_7$)cycloalkyl, (C$_4$-C$_8$)cycloalkyl-alkyl, aryl, aryl(C$_1$-C$_8$)alkyl and (C$_1$-C$_8$)alkylene-Z, wherein Z is selected from the group consisting of COR$^d$, COOR$^d$, NR$^d$R$^e$, NR$^d$CONR$^c$R$^f$, NR$^d$COR$^e$, NR$^d$COOR$^e$ and CONR$^d$R$^e$ wherein R$^d$, R$^e$ R$^f$ are each independently selected from the group consisting of H, (C$_1$-C$_8$)alkyl and phenyl, or optionally two of R$^d$, R$^e$ and R$^f$ when attached to the same nitrogen atom are combined to form a five- or six-membered ring; and wherein R$^m$ is selected from the group consisting of H, (C$_1$-C$_8$)alkyl, aryl and OH, and R$^m$ and R$^c$ are optionally combined with the nitrogen atom to which each is attached to form a five or six membered ring; each of the symbols R$^1$ and R$^3$ represents a member independently selected from the group consisting of halogen, hydroxy, (C$_1$-C$_8$)alkyl, (C$_2$-C$_8$)alkenyl, (C$_2$-C$_8$)alkynyl, (C$_1$-C$_8$) alkoxy, (C$_3$-C$_7$)cycloalkyl, (C$_4$-C$_8$)cycloalkyl-alkyl, (C$_1$-C$_8$) haloalkyl, (C$_1$-C$_8$)heteroalkyl, (C$_2$-C$_5$)heterocyclyl, heterosubstituted(C$_3$-C$_7$)cycloalkyl, heteroalkyl substituted (C$_3$-C$_7$)cycloalkyl, O(C$_1$-C$_8$)haloalkyl, nitro, cyano, phenyl, O-phenyl, NR$^j$-phenyl, S(O)$_r$-phenyl, COR$^j$, COOR$^j$, NR$^j$R$^k$, S(O)$_r$R$^j$, SO$_2$NR$^j$R$^k$, NR$^j$CONR$^k$R$^l$, NR$^j$COR$^k$, NR$^j$COOR$^k$ and CONR$^j$R$^k$ wherein the phenyl ring is optionally substituted and R$^j$, R$^k$ and R$^l$ are each independently selected from the group consisting of H and (C$_1$-C$_8$)alkyl, including (C$_1$-C$_8$)haloalkyl, or optionally two of R$^j$, R$^k$ and R$^l$ when attached to the same nitrogen atom are combined to form a five- or six-membered ring, and the subscript r is an integer of from 0 to 2; the symbol R$^2$ represents a member selected from the group consisting of H and (C$_1$-C$_8$)alkyl; the letter Q represents CH or N; the subscript m is an integer of from 0 to 3; and the subscript p is an integer of from 0 to 2.

In other aspects, the present invention provides pharmaceutical compositions containing one or more of the compounds above, as well as methods of treating a variety of metabolic disorders and conditions using one or more of the compounds provided above.

BRIEF DESCRIPTION OF THE DRAWINGS

Not Applicable.

DETAILED DESCRIPTION OF THE INVENTION

Abbreviations and Definitions

The abbreviations used herein are conventional, unless otherwise defined.

Unless otherwise stated, the following terms used in the specification and claims have the meanings given below:

"Alkyl" refers to a linear saturated monovalent hydrocarbon radical or a branched saturated monovalent hydrocarbon radical having the number of carbon atoms indicated in the prefix. For example, (C$_1$-C$_6$)alkyl is meant to include methyl, ethyl, n-propyl, 2 propyl, tert-butyl, pentyl, and the like. For each of the definitions herein (e.g., alkyl, alkenyl, alkoxy, aralkyloxy), when a prefix is not included to indicate the number of main chain carbon atoms in an alkyl portion, the radical or portion thereof will have six or fewer main chain carbon atoms.

"Alkylene" refers to a linear saturated divalent hydrocarbon radical or a branched saturated divalent hydrocarbon radical having the number of carbon atoms indicated in the prefix. For example, (C$_1$-C$_6$)alkylene is meant to include methylene, ethylene, propylene, 2-methylpropylene, pentylene, and the like.

"Alkenyl" refers to a linear monovalent hydrocarbon radical or a branched monovalent hydrocarbon radical having the number of carbon atoms indicated in the prefix and containing at least one double bond, but no more than three double bonds. For example, (C$_2$-C$_6$)alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, (C$_2$-C$_6$)alkynyl is meant to include ethynyl, propynyl, and the like.

"Alkoxy", "aryloxy", "aralkyloxy", or "heteroaralkyloxy" refers to a radical —OR wherein R is an alkyl, aryl, aralkyl, or heteroaralkyl respectively, as defined herein, e.g., methoxy, phenoxy, benzyloxy, pyridin-2-ylmethyloxy, and the like.

"Aryl" refers to a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^x$R$^y$ (where n is an integer from 0 to 5, R' and R" are independently hydrogen or alkyl, and R$^x$ and R$^y$ are independently selected from hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof.

"Aralkyl" refers to the radical —R$^x$R$^y$ where R$^x$ is an alkylene group (having six or fewer main chain carbon atoms) and $R^y$ is an aryl group as defined above. Thus, "aralkyl" refers to groups such as, for example, benzyl, phenylethyl, 3-(4-nitrophenyl)-2-methylbutyl, and the like. Similarly, "Aralkenyl" means a radical —$R^xR^y$ where $R^x$ is an alkenylene group (an alkylene group having one or two double bonds) and $R^y$ is an aryl group as defined above, e.g., styryl, 3-phenyl-2-propenyl, and the like.

"Arylheteroalkyl" means a radical —$R^xR^y$ where $R^x$ is an heteroalkylene group and $R^y$ is an aryl group as defined herein, e.g., 2-hydroxy-2-phenyl-ethyl, 2-hydroxy-1-hydroxymethyl-2-phenyl-ethyl, and the like.

"Cycloalkyl" refers to a monovalent cyclic hydrocarbon radical of three to seven ring carbons. The cycloalkyl group may have one double bond and may also be optionally substituted independently with one, two, or three substituents selected from alkyl, optionally substituted phenyl, or —$C(O)R^z$ (where $R^z$ is hydrogen, alkyl, haloalkyl, amino, mono-alkylamino, di-alkylamino, hydroxy, alkoxy, or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl, and the like.

"Cycloalkyl-alkyl" means a radical —$R^xR^y$ wherein $R^x$ is an alkylene group and $R^y$ is a cycloalkyl group as defined herein, e.g., cyclopropylmethyl, cyclohexenylpropyl, 3-cyclohexyl-2-methylpropyl, and the like. The prefix indicating the number of carbon atoms (e.g., $C_4$-$C_{10}$) refers to the total number of carbon atoms from both the cycloalkyl portion and the alkyl portion.

"Haloalkyl" refers to an alkyl group which is substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Heteroalkyl" means an alkyl radical as defined herein with one, two or three substituents independently selected from cyano, —$OR^w$, —$NR^xR^y$, and —$S(O)_nR^z$ (where n is an integer from 0 to 2), with the understanding that the point of attachment of the heteroalkyl radical is through a carbon atom of the heteroalkyl radical. $R^w$ is hydrogen, alkyl, cycloalkyl, cycloalkyl-alkyl, aryl, aralkyl, alkoxycarbonyl, aryloxycarbonyl, carboxamido, mono- or di-alkylcarbamoyl. $R^x$ is hydrogen, alkyl, cycloalkyl, cycloalkyl-alkyl, aryl or aralkyl. $R^y$ is hydrogen, alkyl, cycloalkyl, cycloalkyl-alkyl, aryl, aralkyl, alkoxycarbonyl, aryloxycarbonyl, carboxamido, mono- or di-alkylcarbamoyl or alkylsulfonyl. $R^z$ is hydrogen (provided that n is 0), alkyl, cycloalkyl, cycloalkyl-alkyl, aryl, aralkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^w$, $R^x$, $R^y$, and $R^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^w$, —$NR^xR^y$, or —$S(O)_nR^z$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —$(CR'R'')_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —$(CR'R'')_n$—$CONR^xR^y$ (where n is an integer from 0 to 5, R' and R" are independently hydrogen or alkyl, and $R^x$ and $R^y$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —$R^xR^y$ where $R^x$ is an alkylene group and $R^y$ is a heteroaryl group as defined herein, e.g., pyridin-3-ylmethyl, 3-(benzofuran-2-yl)propyl, and the like.

"Heteroaralkenyl" means a radical —$R^xR^y$ where $R^x$ is an alkenylene group and $R^y$ is a heteroaryl group as defined herein, e.g., 3-(pyridin-3-yl)propen-2-yl, and the like.

"Heterocyclyl" or "cycloheteroalkyl" means a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —$(CR'R'')_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —$CR'R''$)"—$CONR^xR^y$ (where n is an integer from 0 to 5, R' and R" are independently hydrogen or alkyl, $R^x$ and $R^y$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of carbon atoms in the portion of the cycloheteroalkyl or heterocyclyl group exclusive of the number of heteroatoms.

"Heterocyclylalkyl" or "Cycloheteroalkyl-alkyl" means a radical —$R^xR^y$ where $R^x$ is an alkylene group and $R^y$ is a heterocyclyl group as defined herein, e.g., tetrahydropyran-2-ylmethyl, 4-methylpiperazin-1-ylethyl, 3-piperidinylmethyl, and the like.

"Heteroalkylene" refers to a linear saturated divalent hydrocarbon radical of one to six carbons or a branched saturated hydrocarbon radical of three to six carbon atoms with one, two or three substituents independently selected from —$OR^w$, —$NR^xR^y$, and —$S(O)_nR^z$ (where n is an integer from 0 to 2) where, $R^w$, $R^x$, $R^y$, and $R^z$ are as defined herein for a heteroalkyl radical. Examples include, 2-hydroxyethan-1,2-diyl, 2-hydroxypropan-1,3-diyl and the like.

"Heterosubstituted cycloalkyl" means a cycloalkyl group wherein one, two, or three hydrogen atoms are replaced by substituents independently selected from the group consisting of cyano, hydroxy, alkoxy, amino, acylamino, mono-alkylamino, di-alkylamino, or —$SO_nR$ (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mono-alkylamino, di-alkylamino, or hydroxyalkyl). Examples include 4-hydroxycyclohexyl, 2-aminocyclohexyl etc.

"Heteroalkyl substituted cycloalkyl" means a cycloalkyl group wherein one, two, or three hydrogen atoms are replaced independently by heteroalkyl groups, with the understanding that the heteroalkyl group is attached to the cycloalkyl group via a carbon-carbon bond. Examples include 1-hydroxymethyl-cyclopent-1-yl, 2-hydroxymethyl-cyclohex-2-yl and the like.

"Heteroalkyl substituted heterocyclyl" means a heterocyclyl group wherein one, two, or three hydrogen atoms are replaced independently by heteroalkyl groups, with the understanding that the heteroalkyl group is attached to the heterocyclyl group via a carbon-carbon bond. Examples include 4-hydroxymethyl-piperidin-1-yl, and the like.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —$(CR'R'')_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R'')_n$—$CONR^xR^y$ (where n is an integer from 0 to 5, R' and R" are independently hydrogen or alkyl, and $R^x$ and $R^y$ are, independently of each other, hydrogen, alkyl, cycloalkyl, cycloalkylalkyl, phenyl or phenylalkyl).

For each of the definitions above, the term "di-alkylamino" refers to an amino moiety bearing two alkyl groups that can be the same, or different.

As used herein, the term "carboxylic acid surrogate" refers to those moieties that are used as surrogates for a carboxylic acid moiety. Such groups are generally known to one of skill in the art (see, for example, THE PRACTICE OF MEDICINAL CHEMISTRY; Wermuth, C. G., ed., Academic Press, New York, 1996, page 203). Suitable isosteres or surrogates include —$C(O)NHSO_2R$ wherein R can be alkyl, haloalkyl, heteroalkyl, aralkyl, aryl, heteroaryl, heterocyclyl, alkoxy, haloalkoxy, aryloxy, alkylamino, haloalkylamino, dialkylamino, dihaloalkylamino, arylamino, diarylamino, arakylamino, diarakylamino or other groups to provide an overall acidic character to the moiety; sulfonic acids; sulfinic acids; phosphonic acids; phosphinic acids; activated sulfonamides (e.g., —$SO_2NHX$ wherein X is an electron withdrawing group relative to an alkyl group, such as an acyl group or aryl group; activated carboxamides (e.g., —$C(O)NHCN$); hydroxamic acids (—$C(O)NHOH$); acidic heterocycles or substituted heterocycles (e.g., tetrazoles, triazoles, hydroxypyrazoles, hydroxyoxazoles, hydroxythiadiazoles); and acidic alcohols (e.g., —$C(CF_3)_2OH$ or —$CH(CF_3)OH$).

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992).

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2 hydroxyethanesulfonic acid, benzenesulfonic acid, 4-chlorobenzenesulfonic acid, 2-napthalenesulfonic acid, 4-toluenesulfonic acid, camphorsulfonic acid, 4 methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

"Prodrugs" means any compound which releases an active parent drug according to Formula 1 in vivo when such prodrug is administered to a mammalian subject. Prodrugs of a compound of Formula 1 are prepared by modifying functional groups present in the compound of Formula 1 in such a way that the modifications may be cleaved in vivo to release the parent compound. Prodrugs include compounds of Formula 1 wherein a hydroxy, amino, or sulfhydryl group in a compound of Formula 1 is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, carbamates (e.g., N,N- dimethylaminocarbonyl) of hydroxy functional groups in compounds of Formula 1, and the like.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991) and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "mammal" includes, without limitation, humans, domestic animals (e.g., dogs or cats), farm animals (cows, horses, or pigs), monkeys, rabbits, mice, and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., *J. Basic & Clin. Phys. & Pharm.* (1998) 9: 387-406 and Flier, J. *Ann Rev. Med.* (1983) 34: 145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plaminogen activator inhibitor-1), has been referred to as "Syndrome X" (see, e.g., Reaven, G. M., *Physiol. Rev.* (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans S. et al., *Diabet. Med.* (1996) (9 Suppl 6): S90-5 and Bell, G. et al., *Annu. Rev. Physiol.* (1996) 58: 171-86; genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenytoin) or inhibit insulin action (e.g., estrogens and glucocorticoids); and diabetes caused by infection (e.g., rubella, Coxsackie, and CMV); as well as other genetic syndromes.

The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, *Diabetes Care,* (1999) Vol 2 (Suppl 1): S5-19).

The term "hyperinsulinemia" refers to the presence of an abnormally elevated level of insulin in the blood. Similarly, the term "hyperuricemia" refers to the presence of an abnormally elevated level of uric acid in the blood. The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "secretagogue" means a substance or compound that stimulates secretion. For example, an insulin secretagogue is a substance or compound that stimulates secretion of insulin.

The term "hemoglobin" or "Hb" refers to a respiratory pigment present in erythrocytes, which is largely responsible for oxygen transport. A hemoglobin molecule comprises four polypeptide subunits (two α chain systems and two β chain systems, respectively). Each subunit is formed by association of one globin protein and one heme molecule which is an iron-protoporphyrin complex. The major class of hemoglobin found in normal adult hemolysate is adult hemoglobin (referred to as "HbA"; also referred to HbA0 for distinguishing it from glycated hemoglobin, which is referred to as "HbA1," described infra) having $\alpha_2\beta_2$ subunits. Trace components such as $HbA_2$ ($\alpha_2\delta_2$) can also be found in normal adult hemolysate.

Among classes of adult hemoglobin HbAs, there is a glycated hemoglobin (referred to as "$HbA_1$" or "glycosylated hemoglobin"), which may be further fractionated into $HbA_{1a1}$, $HbA_{1a2}$, $HbA_{1b}$, and $HbA_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement.

The term "glycosylated hemoglobin" (also referred to as "$HbA_{1c}$", "GHb", "hemoglobin-glycosylated", "diabetic control index" and "glycohemoglobin"; hereinafter referred to as "hemoglobin A1c") refers to a stable product of the nonenzymatic glycosylation of the β-chain of hemoglobin by plasma glucose. Hemoglobin $A_{1c}$, comprises the main portion of glycated hemoglobins in the blood. The ratio of glycosylated hemoglobin is proportional to blood glucose level. Therefore, hemoglobin $A_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin $HbA_{1c}$ can be a good index for carbohydrate metabolism control. Accordingly, blood glucose levels of the last two months can be estimated on the basis of the ratio of $HbA_{1c}$ to total hemoglobin Hb. The analysis of the hemoglobin $A_{1c}$ in blood is used as a measurement enabling long-term control of blood glucose level (see, e.g., Jain, S., et al., *Diabetes* (1989) 38: 1539-1543; Peters A., et al., *JAMA* (1996) 276: 1246-1252).

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels. Similarly, the term "antiuricemic" refers to the lowering of excessive uric acid concentrations in blood to desired levels.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form the low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/ or elevated levels of lipoproteins (e.g., elevated levels of LDL, VLDL and depressed levels of HDL).

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetalipoproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index (BMI) greater than 27.8 kg/m² for men and 27.3 kg/m² for women (BMI equals weight (kg)/height (m²). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172-181; and Knowler, et al., *Am. J. Clin. Nutr.* (1991) 53:1543-1551).

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

General

The present invention derives from the initial discovery that (phenoxy)phenylacetic acids and (pyridyloxy)phenylacetic acids and their analogs, having a trifluoromethyl substituent on each of the aromatic rings, are extremely effective for the treatment of type II diabetes and related metabolic disorders.

Description of the Embodiments

Compounds

In one aspect, the present invention provides compounds having a formula:

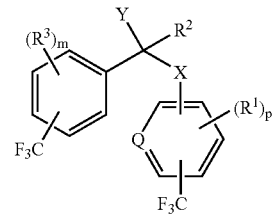

1 or a pharmaceutically acceptable salt thereof, wherein the letter X represents a member selected from the group consisting of O, S, SO, $SO_2$, CHR and NR, wherein R is H, $(C_1-C_8)$alkyl, $COR^a$, $COOR^a$ and $CONR^aR^b$ wherein $R^a$ and $R^b$ are each independently selected from the group consisting of H and $(C_1-C_8)$alkyl; the letter Y represents a member selected from the group consisting of $CH_2OR^c$, $CO_2R^c$, tetrazole, CHO, $CONR^cR^m$, CH(=$NR^c$) and CH(=$NOR^c$), wherein $R^c$ is a member selected from the group consisting of H, $(C_1-C_8)$alkyl, $(C_3-C_8)$alkenyl, $(C_3-C_8)$alkynyl, $(C_3-C_7)$cycloalkyl, $(C_4-C_8)$cycloalkyl-alkyl, aryl, aryl$(C_1-C_8)$alkyl and $(C_1-C_8)$alkylene-Z, wherein Z is selected from the group consisting of $COR^d$, $COOR^d$, $NR^dR^e$, $NR^dCONR^eR^f$, $NR^d$-$COR^e$, $NR^dCOOR^e$ and $CONR^dR^e$ wherein $R^d$, $R^e$ and $R^f$ are each independently selected from the group consisting of H, $(C_1-C_8)$alkyl and phenyl, or optionally two of $R^d$, $R^e$ and $R^f$ when attached to the same nitrogen atom are combined to form a five- or six-membered ring; and wherein $R^m$ is selected from the group consisting of H, $(C_1-C_8)$alkyl, aryl and OH, and $R^m$ and $R^c$ are optionally combined with the nitrogen atom to which each is attached to form a five or six membered ring; each of the symbols $R^1$ and $R^3$ represents a member independently selected from the group consisting of halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-C_8)$haloalkyl, $(C_1-C_8)$heteroalkyl, $(C_2-C_5)$heterocyclyl, heterosubstituted$(C_3-C_7)$cycloalkyl, heteroalkyl substituted $(C_3-C_7)$cycloalkyl, $O(C_1-C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^j$-$CONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from the group consisting of H and $(C_1-C_8)$alkyl, including $(C_1-C_8)$haloalkyl, or optionally two of $R^j$, $R^k$ and $R^l$ when attached to the same nitrogen atom are combined to form a five- or six-membered ring, and the subscript r is an integer of from 0 to 2; the symbol $R^2$ represents a member selected from the group consisting of H and $(C_1-C_8)$alkyl; the letter Q represents CH or N; the subscript m is an integer of from 0 to 3; and the subscript p is an integer of from 0 to 2.

Turning first to the linkage provided in formula 1 as X, preferred groups are O, S and NR. In one group of embodiments, X is O. In another group of embodiments, X is NR, preferably wherein R is H or $(C_1-C_4)$alkyl.

Preferred groups for Y include $CH_2OR^c$, $CO_2R^c$, tetrazole, CHO and $CONR^cR^m$; with $CH_2OR^c$, $CO_2R^c$ and tetrazole being further preferred. The most preferred embodiments are those in which Y is $CH_2OR^c$ or $CO_2R^c$.

Preferred groups for $R^1$ and $R^3$ are halogen, $(C_1-C_8)$alkyl, $(C_1-C_8)$alkoxy, $(C_3-C_7)$cycloalkyl, $(C_4-C_8)$cycloalkyl-alkyl, $(C_1-C_8)$haloalkyl, $O(C_1-C_8)$haloalkyl, nitro, phenyl, O-phenyl, $NR^j$-phenyl, $NR^jCOR^k$, $S(O)_r$-phenyl and $S(O)_rR^j$. Particularly preferred groups for $R^1$ and $R^3$ are halogen, $(C_1-C_8)$alkyl, $(C_1-C_8)$haloalkyl, nitro, O-phenyl, $NR^jCOR^k$ and $S(O)_rR^j$. Still further preferred groups for $R^1$ and $R^3$ are F, Cl, $(C_1-C_4)$alkyl, $CF_3$, $NHCOCF_3$, $NO_2$, $SCH_3$ and $OC_6H_4CF_3$.

The substituent $R^2$ is preferably H or $(C_1-C_4)$alkyl, more preferably H or $CH_3$. In the most preferred embodiments, $R^2$ is H.

The letter Q is preferably CH.

The subscript m is preferably 0 to 2. In one group of embodiments, m is 0. In another group of embodiments, m is 1. In yet another group of embodiments, m is 2.

The subscript p is 0 to 2. In one group of embodiments, p is 0. In another group of embodiments, p is 1. In yet another group of embodiments, p is 2.

Within the above groups of embodiments, certain combinations are also preferred. Turning first to the embodiments in which Q is CH, X is preferably O, S or NR. Still further preferred are those embodiments in which Y is $CO_2R^c$. Even further preferred are those embodiments in which m is 0 to 2 and p is 0 to 1. Within the group of embodiments in which Q is CH, X is O, S or NR, Y is $CO_2R^c$, m is 0 to 2 and p is 0 to 1, the symbol $R^1$ will preferably represent halogen, nitro, $(C_1-C_8)$alkyl, $(C_1-C_8)$alkoxy, or $(C_1-C_8)$haloalkyl. Returning to the group of embodiments in which Q is CH, X is O, S or NR, Y is $CO_2R^c$, m is 0 to 2 and p is 0 to 1, the symbol $R^3$ will preferably represent halogen, nitro, $(C_1-C_8)$alkyl, $(C_1-C_8)$alkoxy, or $(C_1-C_8)$haloalkyl. For those embodiments in which two $R^3$ groups are present, it is understood that each $R^3$ group is independently selected from the provided list. For each of these groups of embodiments, including those in which $R^1$ and $R^3$ are provided with their full scope according to formula I above, the symbol $R^c$ is preferably H, $(C_1-C_8)$ alkyl or $(C_1-C_8)$alkylene Z. Further preferred are those embodiments in which $R^2$ is H or $CH_3$.

In one group are particularly preferred embodiments, Q is CH; X is selected from the group consisting of O and NR; Y is selected from the group consisting of $CH_2OR^c$ and $CO_2R^c$; the subscript m is 0 to 2 and the subscript p is 0 to 1; each $R^1$ is selected from the group consisting of halogen, nitro, $(C_1-C_8)$ alkyl and $(C_1-C_8)$ alkoxy; each $R^3$ is selected from the group consisting of halogen, nitro, $(C_1-C_8)$ alkyl and $(C_1-C_8)$ alkoxy; and $R^2$ is H or $CH_3$. Selected groups of embodiments within the above are those in which (i) X is O and Y is $CO_2R^c$; (ii) X is O and Y is $CH_2OR^c$; (iii) X is NH and Y is $CO_2R^c$; (iv) X is NH and Y is $CH_2OR^c$. Still further preferred embodiments for each of these group are those in which $R^1$ and $R^3$ are selected from F, Cl, $(C_1-C_4)$alkyl, $CF_3$, $NHCOCF_3$, $NO_2$, $SCH_3$ and $OC_6H_4CF_3$.

Preparation of the Compounds

Compounds 1 in which Y is $CO_2R^c$ and X is O, S or NH are prepared as shown in Scheme 1a and 1b. Compounds 1 in which X is C are prepared as shown in Scheme 1c.

An alternative method for introducing the substituent $R^1$ is shown in Scheme 1d, and routes for preparing the aldehydes (1, Y=CHO), carbinols (1, Y=$CH_2OH$) and carbinol esters (1, Y=$CH_2OCOR^c$) are shown in Scheme 1e.

The preparation of Compound 1 in which Y is tetrazole is shown in Scheme 1f, 1g.

Compounds 1 in which Y=$COOR^c$ and $R^c$ is H can be converted into compounds 1 in which $R^c$ is alkyl or aralkyl using conventional esterification procedures, for example as described in Preparative Organic Chemistry, by R. B. Wagner and H. D. Zook, Wiley, p 479.

Scheme 1 - Preparation of Compounds 1

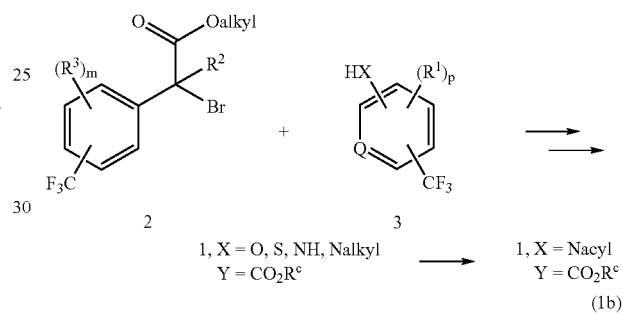

(1a)

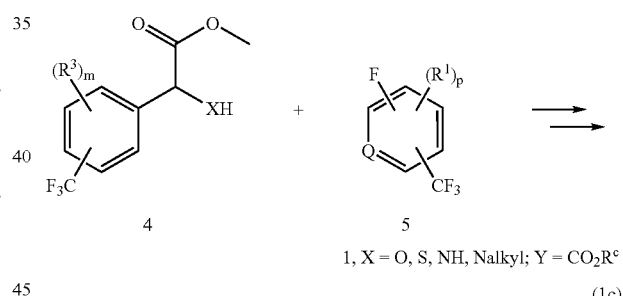

(1b)

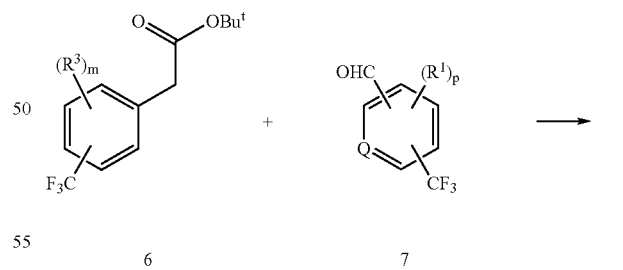

(1c)

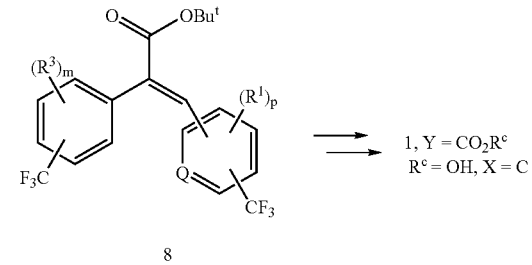

-continued
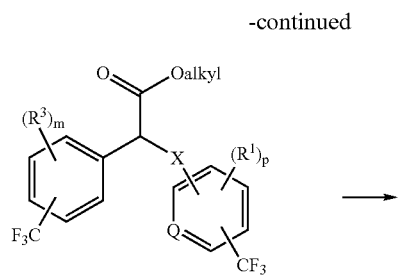
1, Y = CO$_2$R$^c$
R$^2$ = H
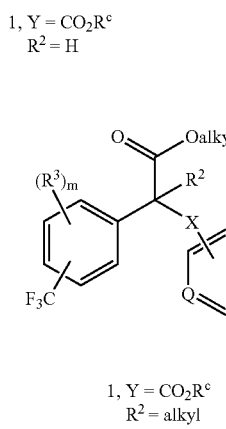
1, Y = CO$_2$R$^c$
R$^2$ = alkyl
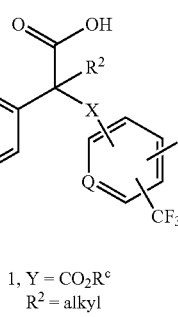
1, Y = CO$_2$R$^c$
R$^2$ = alkyl
(1e)
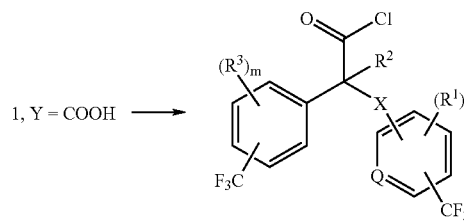
1, Y = COOH
9
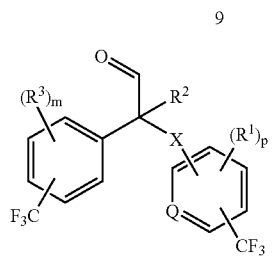
1, Y = CHO
-continued
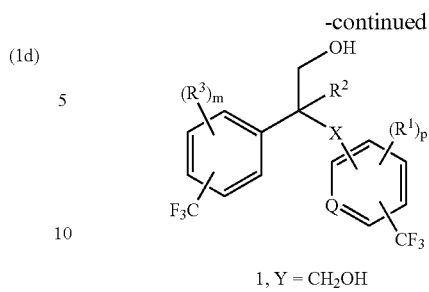
1, Y = CH$_2$OH
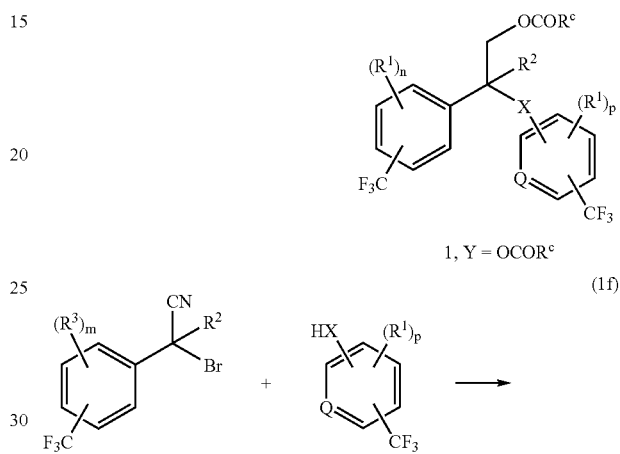
1, Y = OCOR$^c$
(1f)
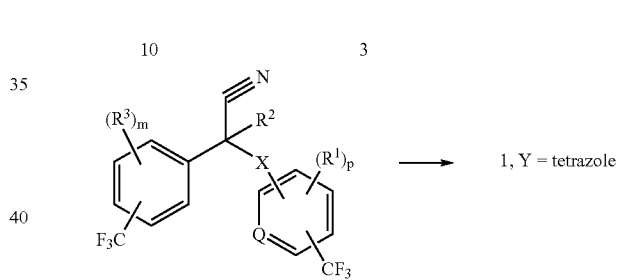
10  3
1, Y = tetrazole
11
(1g)
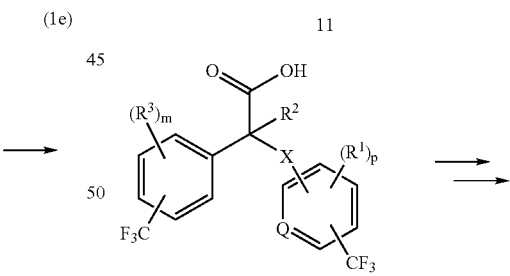
1 Y = COOH
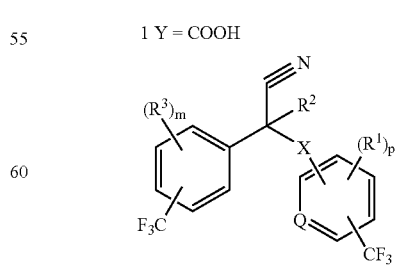
11

-continued

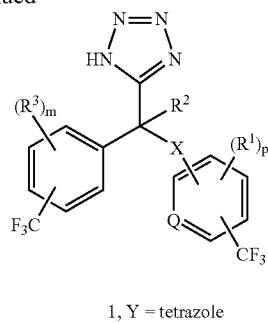

1, Y = tetrazole

Displacement of Benzylic Bromides with Nucleophiles

As illustrated in Scheme 1a, the bromoesters 2 are reacted with the phenols, amines or mercaptans 3, to afford the products 1. The reaction is conducted in a polar aprotic solvent such as tetrahydrofuran or, preferably, dimethylformamide, in the presence of a base such as diazabicyclononene or, preferably, potassium carbonate. The products 1 in which X is NH can be converted into the products in which N is acyled by a conventional acylation reaction, for example by reaction with an acyl chloride or anhydride in a basic solvent such as pyridine.

Displacement of Fluorine Substituents with Phenylacetic Ester Nucleophiles

Scheme 1b illustrates the synthesis of the products 1 by means of a fluorine displacement reaction. The carbinols, mercaptans, or amines 4, X=O, S, NH or N-alkyl are reacted with a fluorine-substituted benzene or pyridine moiety 5. In this reaction, the substrates 4 are first converted into an alkali metal salt, by treatment with a base such as sodium hydride or sodium hexamethyldisilazide. The reaction is conducted in an aprotic polar solvent such as tetrahydrofuran or dimethylformamide. The aryl fluoride 5 is then added, and the reaction proceeds to afford the products, X=O, S, NH or Nalkyl.

Condensation Reactions of Aldehydes 7 with Phenylacetic Esters 6

Scheme 1c illustrates the synthesis of compounds 1 in which X is C. In this procedure, the tert-butyl esters 6 are first reacted with a base such as sodium hydride, in an aprotic solvent such as dimethylformamide. The anion generated is reacted with the aldehydes 7. After dehydration, the unsaturated products 8 are obtained. These compounds are converted into the products 1, X=C, by means of catalytic hydrogenation, using, for example, 5% palladium on carbon as catalyst.

Alkylation Reactions to Introduce Substituents $R^2$

Scheme 1d illustrates the introduction of the alkyl substituents $R^2$ by means of an alkylation reaction. In this procedure, the esters 1 are first reacted with a base such as sodium hydride or sodium hexamethyldisilazide, in an aprotic solvent such as tetrahydrofuran or dimethylformamide. An alkylating agents $R^2Br$ or $R^2I$ is then added, and the reaction proceeds to yield the ester products 1, in which Y is carboxyl ester and $R^2$ is alkyl. Basic hydrolyis, for example by the use of lithium hydroxide in aqueous tetrahydrofuran, affords the carboxylic acids 1 in which $R^2$ is alkyl.

Preparation of Aldehyde and Carbinol Derivatives 1

Scheme 1e illustrates methods for preparing compounds 1 in which Y is CHO, $CH_2OH$ and $CH_2OCOalkyl$. The compounds 1, Y=COOH, are first converted into the acid chlorides 9, by reaction with oxalyl chloride or, preferably, thionyl chloride. The acid chlorides 9 are then hydrogenated in the presence of a 5% palladium on barium carbonate catalyst, as described in *Journal of the American Chemical Society*, 108:2608 (1986), to afford the aldehydes 1, Y=CHO. Alternatively, the acid chlorides 9 can be converted into the corresponding aldehydes by reduction employing lithium tri-tertiarybutyl aluminum hydride, as described in *Journal of the American Society*, 79:252 (1956). The latter compounds are converted into the corresponding carbinols 1, Y=$CH_2OH$, by means of a reduction reaction, for example by treatment with sodium borohydride in ethanol or isopropanol. The products 1, Y=$CH_2OH$ are transformed into the esters 1, Y=$CH_2OCOalkyl$, by means of acylation reactions, for example by reaction with acetyl chloride in a basic solvent such as pyridine.

Preparation of Tetrazole Derivatives 1

Scheme 1f illustrates methods for preparing compounds 1 in which Y is tetrazole. The bromonitriles 10 are reacted with the phenols, amines or mercaptans 3, to afford the intermediate 11. The reaction is conducted in a polar aprotic solvent such as tetrahydrofuran or, preferably, dimethylformamide, in the presence of a base such as diazabicyclononene or, preferably, potassium carbonate. The intermediate 11 is then converted into the tetrazole with an azide or, preferably trimethyltin azide. Alternatively, intermediate 11 can be prepared from compound 1 (Y=COOH) by first transforming the acid into an amide and followed by dehydration (Scheme 1g).

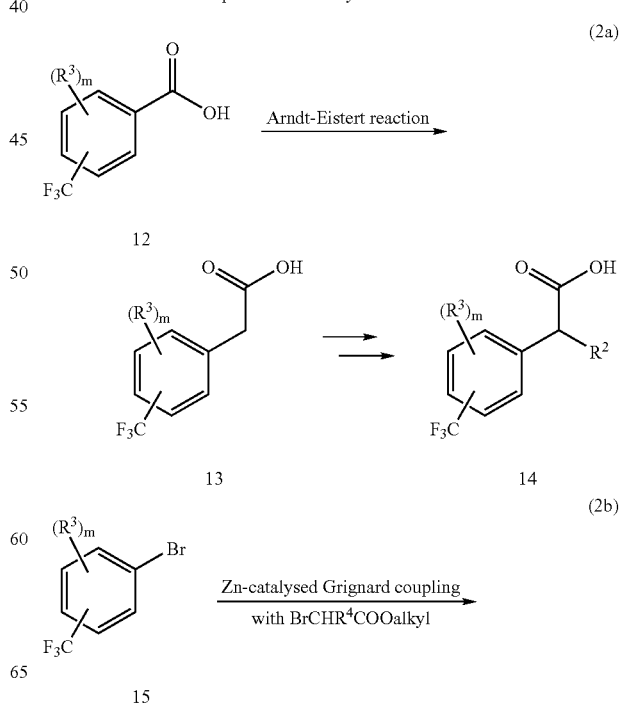

-continued

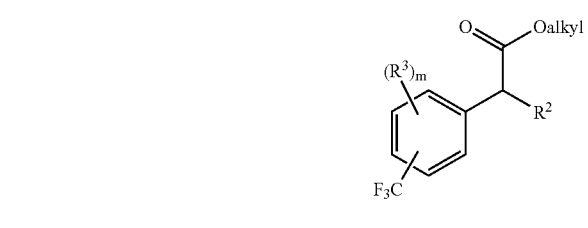
6

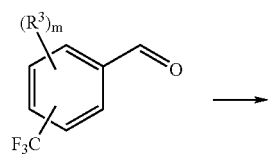
16

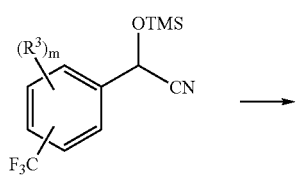
17

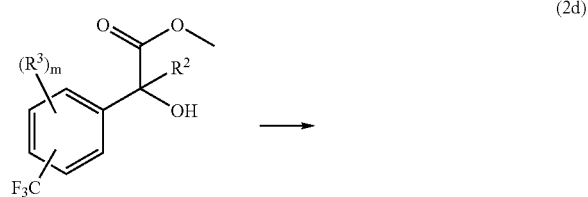
18    19

(2d)

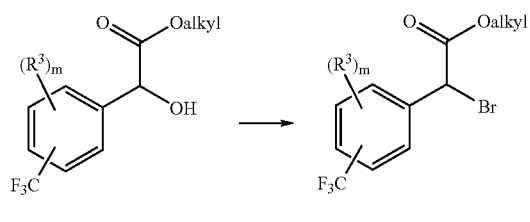
4

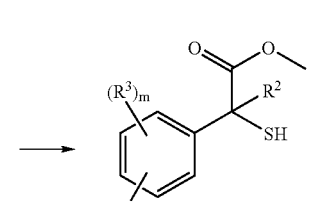
20    4, X = S

-continued

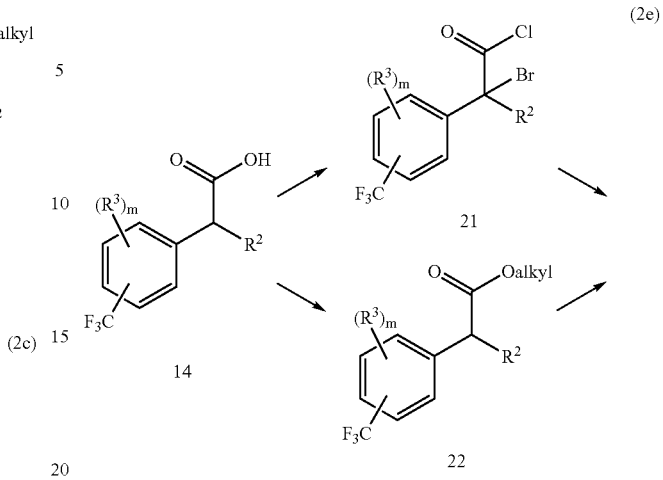
14    21

22

(2e)

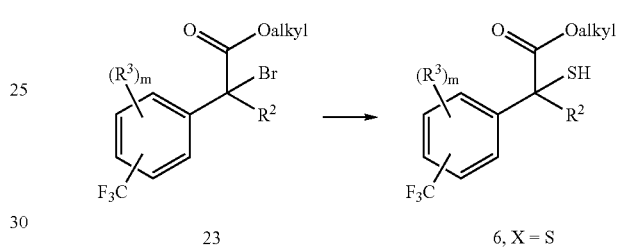
23    6, X = S

Phenylacetic Acid and Phenyl Acetonitrile Starting Materials for the Preparation of Compounds 1

Many variously substituted phenylacetic acids, and precursors therefor, are commercially available or are described in the literature. In addition, a number of synthetic routes are available to prepare compounds not previously reported. Scheme 2 shows some synthetic routes to variously substituted phenylacetic acids and derivatives thereof.

Scheme 2a illustrates the Arndt-Eistert reaction, as described in *Journal of the American Chemical Society*, 72:5163 (1950), whereby variously substituted benzoic acids can be transformed into the corresponding phenylacetic acids. In this procedure the benzoic acid is first transformed into the acid chloride by treatment with oxalyl chloride or thionyl chloride. The acid chloride is then reacted with an excess of diazomethane, and the resulting diazoketone is rearranged by treatment with a silver salt, for example silver benzoate, at reflux in an alcohol such as methanol, to afford the corresponding ester of the product 13. The free acid 13 can then be obtained by basic hydrolysis.

Alternatively, the ester of 13 can be alkylated, for example by treatment with a strong base such as lithium diisopropylamide, followed by reaction with a halide $R^2X$, to afford after basic hydrolysis the alkylated phenylacetic acids 14.

Scheme 2b illustrates the conversion of various bromobenzenes into the corresponding phenylacetic, phenylpropionic acids etc. In this procedure, the substituted bromobenzene 15 is first reacted with magnesium in an ethereal solvent such as tetrahydrofuran, to form a Grignard reagent. An equimolar amount of anhydrous zinc chloride is then added, followed by addition of ethyl bromoacetate, to afford after basic hydrolysis the appropriately substituted phenylacetic acid 6, $R^2$+H. Compounds 6 in which $R^2$ is methyl, ethyl etc can be obtained by employing ethyl 2-bromopropionate, or ethyl 2-bromobutyrate, etc, in place of ethyl bromoacetate.

Scheme 2c illustrates the conversion of variously substituted benzaldehydes into the α-bromophenylacetic acid eaters. In this procedure, which is described in *Synthetic Communications*, 12:763 (1982), the benzaldehyde is first reacted with trimethylsilylcyanide in the presence of potassium cyanide and a crown ether, to afford the correspondingly substituted α-(trimethylsilyloxy)phenylacetonitriles 17. These products are then treated with an alcohol in the presence of an acid catalyst to produce the α-hydroxyphenylacetic esters 18. Reaction of the latter compounds with a brominating agent such as triphenyl phosphine/carbon tetrabromide, as described in *Tetrahedron Letters*, 28:3225 (1987), affords the bromoesters 19.

Scheme 2d illustrates the conversion of variously substituted α-hydroxyphenylacetic esters into the corresponding α-bromo and α-mercaptophenylacetic esters 20 and 4, X=S. In this procedure, the α-hydroxyphenylacetic esters 4 are first converted to the corresponding α-bromo esters, as described above. The bromoesters 20 are then reacted with a sulfur nucleophile, such as sodium thiolacetate to afford the corresponding α-mercaptophenylacetic esters 4, X=S.

Scheme 2e illustrates alternative methods to prepare the α-bromo and α-mercaptophenylacetic esters 23 and 4, X=S, from the corresponding phenylacetic acids 14. In this procedure, the acids 14 are first treated with bromine and thionyl chloride, to afford the α-bromo acid chlorides 21. Upon treatment with an alcohol, these compounds are converted into the α-bromophenylacetic esters 23. Alternatively, the phenylacetic acids 14 are first converted into the esters 22, using conventional esterification procedures. The esters 22 are then reacted with a brominating agent such as bromine or N-bromosuccinimide, to afford the α-bromophenylacetic esters 23. These compounds can be transformed into the α-mercaptophenylacetic esters 4, X=S, as described previously.

All phenyl acetic acids can be transformed the corresponding phenyl acetonitriles by standard transformations (see Scheme 1g).

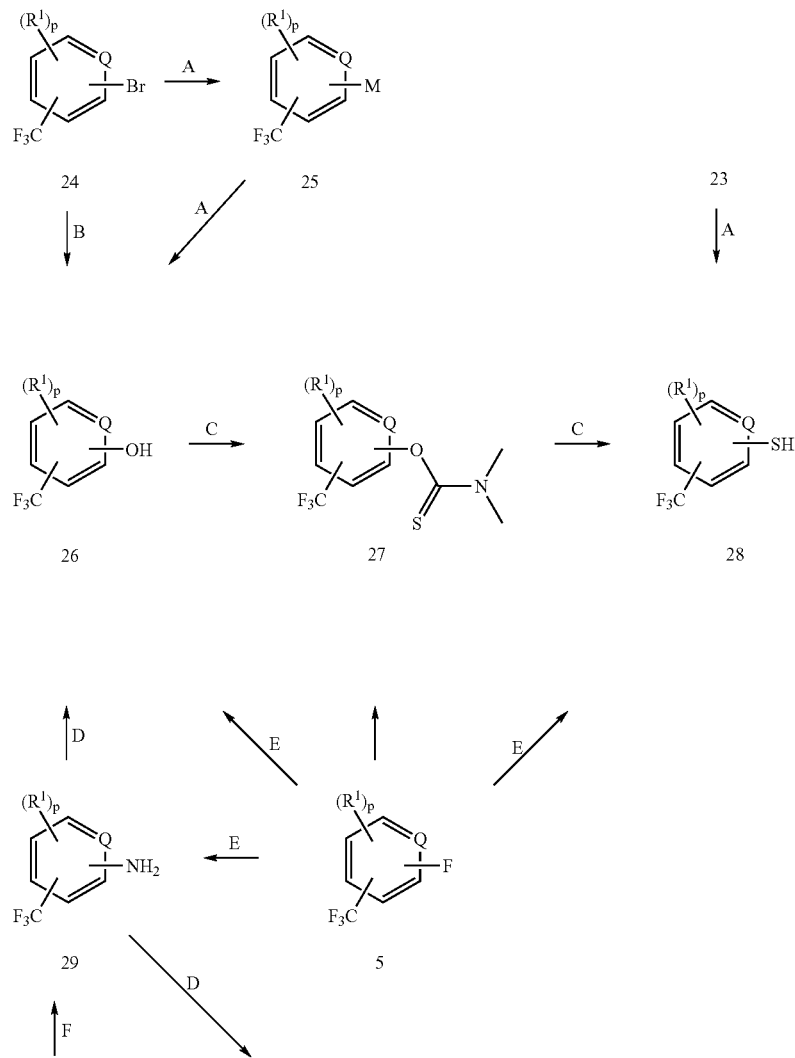

Scheme 3 - Preparations and interconversions of phenols, amines, mercaptans and aldehydes

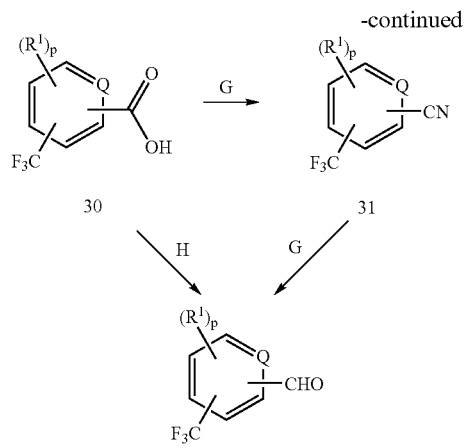

Phenol, Thiol, Amine and Aldehyde Starting Materials for the Preparation of Compounds 1

Many phenols, thiols, amines and aldehydes required for the preparation of the compounds of this invention are commercially available or have been described in the literature. In addition, a number of synthetic routes are available to prepare compounds not previously made. In Scheme 3 are shown some synthetic routes to, and interconversions among, the compounds.

Route A represents the synthesis of phenols from the corresponding bromo compounds 24. In this route, the bromo compound is first converted into an organolithium or organomagnesium derivative 25, respectively by reaction with an alkyllithium such as n-butyllithium, or with magnesium metal. The compound 25 is then converted to the phenol 26 either by direct oxidation using, for example, molybdenum pentoxide, as described in *Journal of Organic Chemistry*, 42:1479 (1979), or by reaction first with a trialkylborate followed by oxidation with hydrogen peroxide, as described in *Journal of Organic Chemistry*, 24:1141 (1959).

Route B represents the conversion of the bromo compounds 24 directly to the phenols 26 or thiophenols 28. This reaction proceeds in the case of particularly reactive bromo compounds, for example, 2- or 4-bromopyridines, (24, Y=N). The reaction can be effected by treatment of the bromopyridine with aqueous acid or base, as described in *Rec. Trav. Chim.*, 59:202 (1940). The thiols corresponding to 26 are produced by reaction of the reactive bromo compound with sodium sulfide in an alcoholic solvent such as ethanol, as described in *Rec. Trav. Chim.*, 64:102 (1945).

Route C represents the conversion of a phenol 26 into the corresponding thiol 27. In this procedure, described in *Journal of Organic Chemistry*, 81:3980 (1966), the phenol is first reacted with dimethylthiocarbamoyl chloride, to afford the intermediate thiocarbamate 28, which upon thermal rearrangement followed by basic hydrolysis, affords the thiol 29.

Route D represents the preparation of phenols 26 and cyano compounds 31 from the corresponding amine by a diazotization procedure, as described in *Organic Syntheses, Collective volume* 3, 130, 1955. In this reaction, the amine is reacted with nitrous acid to afford the diazonium salt, which upon acidic hydrolysis yields the phenol 26. Alternatively, the diazonium salt can be reacted with cuprous cyanide or nickel cyanide, as described in *Organic Functional Group Preparations*, by S. R. Sandler and W. Karo, Academic press, New York, p 463 to afford the cyano compound 31. The cyano compound is useful for the preparation of the corresponding aldehyde 7.

Route E represents the conversion of the fluoro compound 5 to either the phenols 26, the thiols 28 or the amines 29. In this procedure, the fluoro compound is reacted with, for example, sodium methoxide, to afford the corresponding methoxyl-substituted product. The methoxyl group is then removed, using, for example, boron tribromide or aluminum chloride, to afford the phenol 26. Alternatively, the fluoro compound 5 is reacted with a nitrogen nucleophile, such as, for example, sodium azide, to afford the corresponding azidobenzene. Reduction of the azido group, for example by the use of lithium aluminum hydride, affords the amino compound 29. The thiols 28 are obtained by reaction of the fluoro compounds 5 with a sulfur nucleophile, for example with ethanolic sodium sulfide.

Route F represents the conversion of the carboxylic acids 30 to the amines 29 via the Curtius rearrangement as described in *Organic Syntheses, Collective Volume* 4, 819, 1963. In this procedure, the carboxylic acid is first converted into the acid chloride by reaction with thionyl chloride. The acid chloride is treated with sodium azide to afford the acyl azide, which upon thermal rearrangement in aqueous solution affords the amines 29.

Route G represents the conversion of the carboxylic acids 30 into the aldehydes 7 via corresponding nitrile 31. The conversion of the carboxylic acids 30 into the nitriles 31 can be effected in a number of ways, as described in Comprehensive Organic Transformations, by R. C. Larock, VCH Publishers, 1989, p 963ff. For example, the carboxylic acid can first be converted into the acid chloride, and the latter compound is then reacted with ammonia to afford the corresponding amide. Treatment of the amide with, for example, p-toluenesulfonyl chloride in pyridine, then affords the nitrile 31. The nitrile can then be reduced to afford the aldehyde 7, for example by employing diisobutylaluminum hydride, as described in *Journal of the American Chemical Society*, 107:7524 (1985).

Route H represents the conversion of the carboxylic acids 30 into the corresponding aldehydes 7. This conversion can be effected in a number of ways, as described in Comprehensive Organic Transformations, by R. C. Larock, VCH Publishers, 1989, p 619ff. For example, the carboxylic acid can be first converted into the acid chloride, as described above. The latter compound can then be hydrogenated, using a catalyst of palladium on barium carbonate, as described in *Journal of the American Chemical Society,* 108:2608 (1986), or by reduction using lithium aluminum tri-tertiarybutoxy hydride, as described in *Journal of the American Chemical Society,* 79:252 (1956) to afford the aldehydes 7.

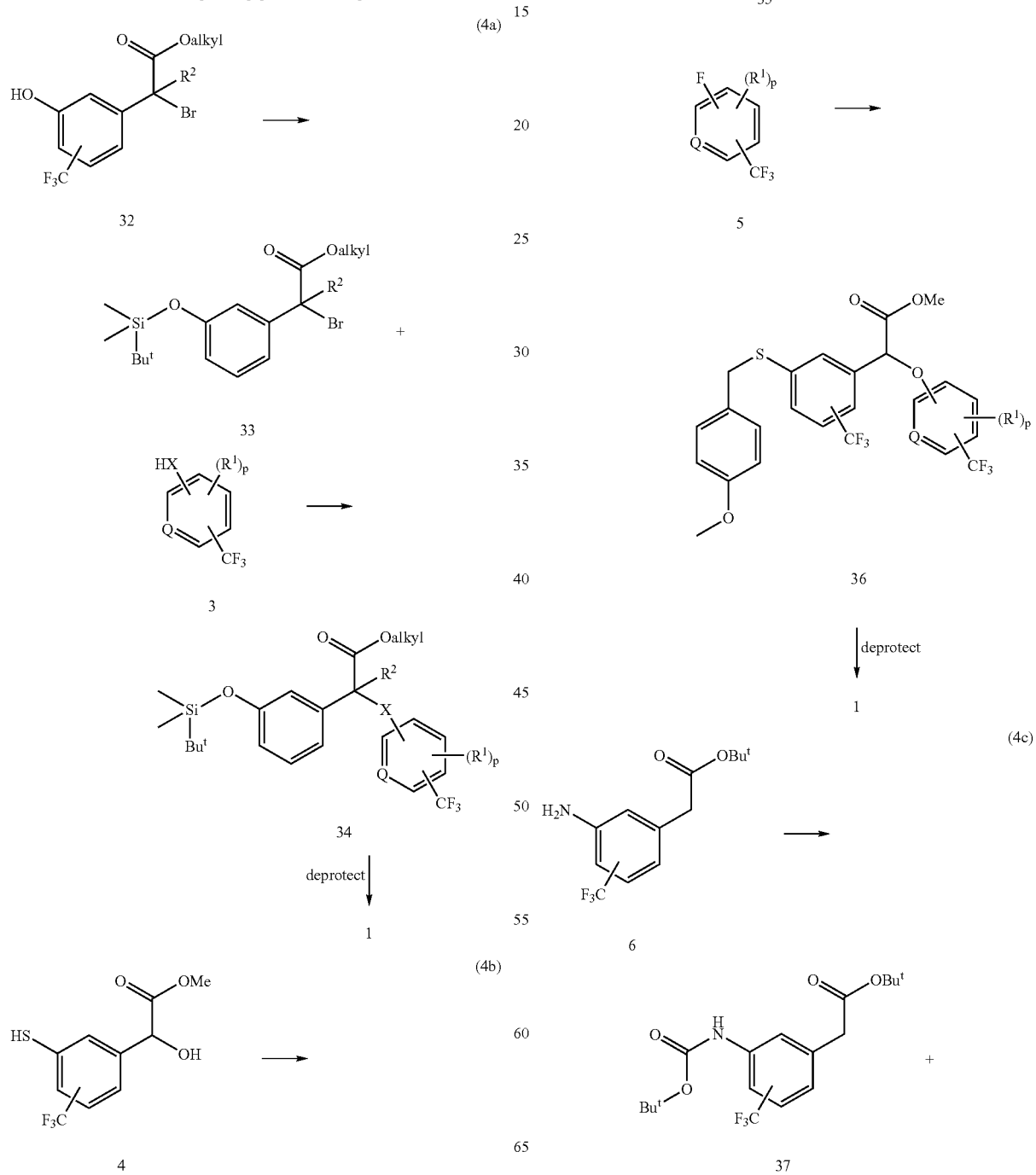

-continued

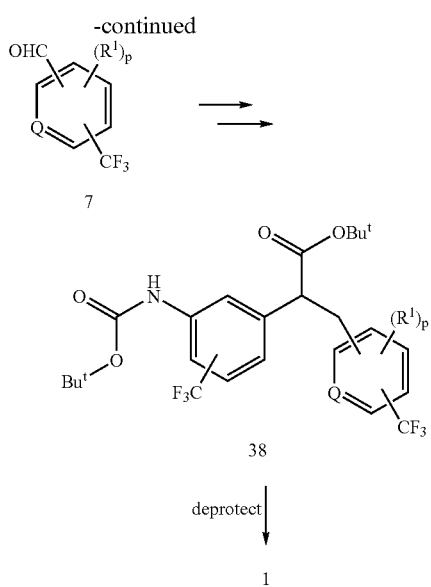

deprotect

1

Protection and Deprotection of Reactive Groups During Syntheses

The phenylacetic acid derivatives 2, 4 and 6 may contain reactive groups such as OH, SH and $NH_2$ which could undergo unwanted reactions during synthetic procedures. Such groups may, according to the judgement of one skilled in the art, require protection before a given synthetic step, and deprotection after the synthetic step. Scheme 4 shows examples of protection and deprotection. The choice, attachment and removal of protective groups is described, for example, in PROTECTIVE GROUPS IN ORGANIC SYNTHESIS, by T. W. Greene and P. G. M. Wuts, Wiley, 1991.

Scheme 4a illustrates the protection of a hydroxyl substituted phenylacetic acid derivative 32. The compound is reacted with tert-butylchlorodimethylsilane in the presence of imidazole to afford the silyl ether 33. After reaction, as described above, with the intermediate 3, to afford the protected product 34, the protective group is removed by treatment with tetrabutyl ammonium fluoride, to afford the final product 1. The silylation/desilylation procedures are described in PROTECTIVE GROUPS IN ORGANIC SYNTHESIS, by T. W. Greene and P. G. M. Wuts, Wiley, 1991, p 145.

Scheme 4b illustrates the protection of a mercapto-substituted phenylacetic acid derivative 4. The compound is reacted with 4-methoxybenzyl chloride, to afford the thioether 35. This compound is reacted, as described above, with the intermediate 5, to afford the coupled product 36. Deprotection, employing mercuric acetate in trifluoroacetic acid, then affords the final product 1. The benzylation/debenzylation procedures are described in PROTECTIVE GROUPS IN ORGANIC SYNTHESIS, by T. W. Greene and P. G. M. Wuts, Wiley, 1991, p 281.

Scheme 4c illustrates the protection of an amino-substituted phenylacetic acid derivative 6. The compound is reacted with tert-butoxycarbonyl chloride, to afford the carbamate 37. After condensation with the aldehyde 7, as described above, and subsequent dehydration/hydrogenation steps, the intermediate 36 is obtained. Deprotection, using trifluoroacetic acid, then affords the final product 1.

The silylation/desilylation procedures are described in PROTECTIVE GROUPS IN ORGANIC SYNTHESIS, by T. W. Greene and P. G. M. Wuts, Wiley, 1991, p 327.

Preparation of Individual Enantiomers of Compounds 1.

Individual enantiomers of those compounds 1 can be separated by a number of methods well known to those skilled in the art. For example, racemic carboxylic acids 1 can be converted into salts with a chiral amine, such as, for example quinine, cinchonidine and the like. Fractional crystallization of the resultant salt, followed by release of the resolved acids, then affords chiral 1. Alternatively, chiral carboxylic acids can be converted into amides with chiral amines, such as, for example, (R) or (S) 1-phenylethylamine. The resultant diastereomeric amides can then be separated by chromatography, and the chiral acids regenerated by hydrolysis. Alternatively, racemic compounds 1 can be separated into individual enantiomers by chiral HPLC.

In addition, the racemic phenylacetic acid precursors of the compounds 1 can be separated into individual enantiomers, using, for example, the methods described above, prior to the formation of the compounds 1.

Scheme 5 - Nomenclature

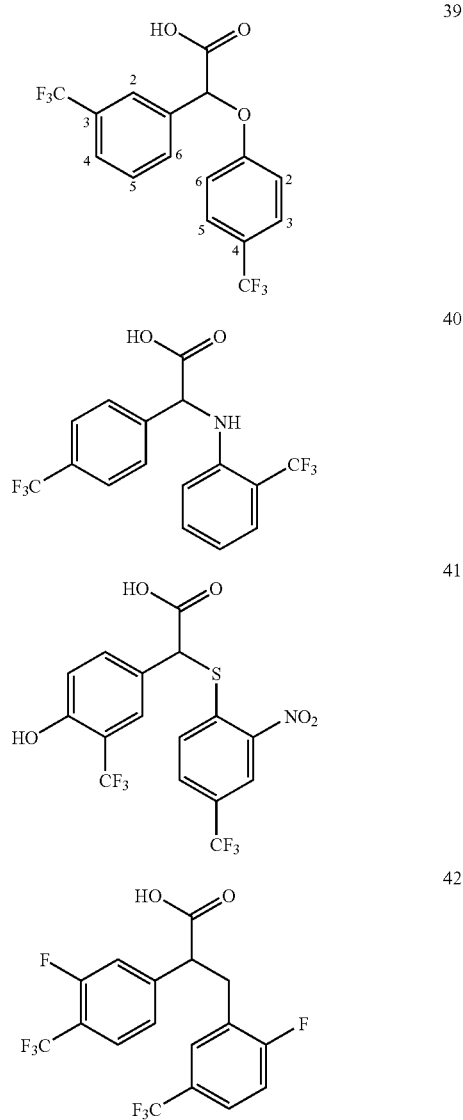

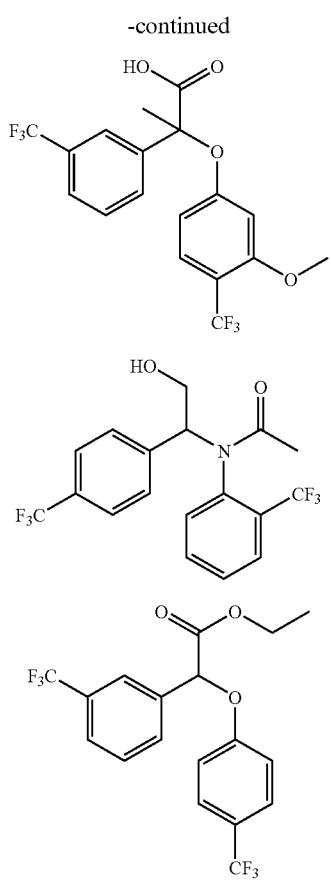

Nomenclature

The compounds of this invention are named as derivatives of phenylacetic acids. Compounds 1 in which X is O, S or NH are respectively named as phenoxy, phenylsulfanyl or phenylamino phenylacetic acids. Compounds in which X is C are named as derivatives of phenylpropionic acid. Scheme 5 shows representative compounds of this invention. The numbering system for substituents is shown on compound 39.

The names of the representative structures of Scheme 5 are as follows: 39 (4-Trifluoromethyl-phenoxy)-(3-trifluoromethyl-phenyl)-acetic acid; 40 (4-Trifluoromethyl-phenyl)-(2-trifluoromethyl-phenylamino)-acetic acid; 41 (4-Hydroxy-3-trifluoromethyl-phenyl)-(2-nitro-4-trifluoromethyl-phenylsulfanyl)-acetic acid; 42 2-(3-Fluoro-4-trifluoromethyl-phenyl)-3-(2-fluoro-5-trifluoromethyl-phenyl)-propionic acid; 43 2-(3-Methoxy-4-trifluoromethyl-phenoxy)-2-(3-trifluoromethyl-phenyl)-propionic acid; 44 N-[2-Hydroxy-1-(4-trifluoromethyl-phenyl)-ethyl]-N-(2-trifluoromethyl-phenyl)-acetamide; 45 (4-Trifluoromethyl-phenoxy)-(3-trifluoromethyl-phenyl)-acetic acid ethyl ester. Names generated by Autonom.

Pharmaceutical Compositions and Methods of Treating Diseases and Conditions

In accordance with the present invention, a therapeutically effective amount of a compound of formula 1 can be used for the preparation of a pharmaceutical composition useful for treating an inflammatory condition, treating diabetes, treating hyperlipidemia, treating hyperuricemia, treating obesity, lowering triglyceride levels, lowering cholesterol levels, raising the plasma level of high density lipoprotein, and for treating, preventing or reducing the risk of developing atherosclerosis.

The compositions of the invention can include compounds of formula 1, pharmaceutically acceptable salts thereof, or a hydrolyzable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of Type 2 diabetes.

The compounds of formula 1 that are used in the methods of the present invention can be incorporated into a variety of formulations for therapeutic administration. More particularly, the compounds of formula 1 can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local rather than systemic manner, in a depot or sustained release formulation. In addition, the compounds can be administered in a liposome.

The compounds of formula 1 can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. Compounds of formula 1 can be administered alone, in combination with each other, or they can be used in combination with other known compounds (see Combination Therapy below).

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of formula 1 can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics*, Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 100 mg to about 3000 mg of the active compound. A preferred unit dose is between 500 mg to about 1500 mg. A more preferred unit dose is between 500 to about 1000 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

Combination Therapy

As noted above, the compounds of the present invention will, in some instances, be used in combination with other therapeutic agents to bring about a desired effect. Selection of additional agents will, in large part, depend on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W.,(ed.), CURRENT THERAPY IN ENDOCRINOLOGY AND METABOLISM, $6^{th}$ Edition (Mosby-Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. *Am. J. Cardiol* (1998) 82(12A): 3U-17U). These studies indicate that diabetes and hyperlipidemia modulation can be further improved by the addition of a second agent to the therapeutic regimen. Combination therapy includes administration of a single pharmaceutical dosage formulation which contains a compound having the general structure of formula 1 and one or more additional active agents, as well as administration of a compound of formula 1 and each active agent in its own separate pharmaceutical dosage formulation. For example, a compound of formula 1 and an HMG-CoA reductase inhibitor can be administered to the human subject together in a single oral dosage composition, such as a tablet or capsule, or each agent can be administered in separate oral dosage formulations. Where separate dosage formulations are used, a compound of formula 1 and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated) atherosclerosis, wherein a compound of formula 1 is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of formula 1 can be administered in combination with more than one additional active agent, for example, a combination of a compound of formula 1 with an HMG-CoA reductase inhibitor (e.g., lovastatin, simvastatin and pravastatin) and aspirin, or a compound of formula 1 with an HMG-CoA reductase inhibitor and a β blocker.

Another example of combination therapy can be seen in treating obesity or obesity-related disorders, wherein the compounds of formula 1 can be effectively used in combination with, for example, phenylpropanolamine, phentermine, diethylpropion, mazindol; fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders wherein the compounds of formula 1 can be effectively used in combination with, for example, neuropeptide Y, enterostatin, cholecytokinin, bombesin, amylin, histamine H3 receptors, dopamine $D_2$ receptors, melanocyte stimulating hormone, corticotrophin releasing factor, galanin and gamma amino butyric acid (GABA).

Still another example of combination therapy can be seen in modulating diabetes (or treating diabetes and its related symptoms, complications, and disorders), wherein the compounds of formula 1 can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

A further example of combination therapy can be seen in modulating hyperlipidemia (treating hyperlipidemia and its related complications), wherein the compounds of formula 1 can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

Additionally, an effective amount of a compound of formula 1 and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, $β_3$ adrenergic receptor agonists; sulfonylureas, biguanides, α-glucosidase inhibitors, other insulin secretogogues, and insulin can be used together for the preparation of a pharmaceutical composition useful for the above-described treatments.

Kits

In addition, the present invention provides for kits with unit doses of the compounds of formula 1, either in oral or injectable doses. In addition to the containers containing the unit doses will be an informational package insert describing the use and attendant benefits of the drugs in alleviating symptoms and/or complications associated with Type 2 diabetes as well as in alleviating hyperlipidemia and hyperuricemia, or for alleviating conditions dependent on PPAR. Preferred compounds and unit doses are those described herein above.

For the compositions, methods and kits provided above, one of skill in the art will understand that preferred compounds for use in each are those compounds that are preferred above and particularly those compounds provided in the Examples below.

EXAMPLES

Experimental Section

General Methods. All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on E. Merck silica gel 60 (240-400 mesh) according to the protocol of Still, Kahn, and Mitra (*J. Org. Chem.* 1978, 43, 2923). Thin layer chromatography was performed using precoated plates purchased from E. Merck (silica gel 60 $PF_{254}$, 0.25 mm) and spots were visualized with long-wave ultraviolet light followed by an appropriate staining reagent.

Nuclear magnetic resonance (NMR) spectra were recorded on a Varian Inova-400 resonance spectrometer. $^1$H NMR chemical shifts are given in parts per million (δ) downfield from tetramethylsilane (TMS) using TMS or the residual solvent signal ($CHCl_3$=δ 7.24, DMSO=δ 2.50) as internal standard. $^1$H NMR information is tabulated in the following format: number of protons, multiplicity (s, singlet; d, doublet; t, triplet; q, quartet; m, multiplet), coupling constant(s) (J) in hertz, and, in selected cases, position assignment. The prefix app is occasionally applied in cases where the true signal multiplicity was unresolved and br indicates the signal in question was broadened.

Combustion analyses were performed by Robertson Microlit Laboratories, Inc. (Madison, N.J., USA) and optical rotations were measured on Perkin-Elmer 241 MC polarimeter and reported as: $[α]^T λ$(c=(g/100 mL), solvent). Melting points were measured on a Fisher-Johns 12-144 apparatus and uncorrected.

Preparation 1.
Bromo-(2-chloro-5-trifluoromethyl-phenyl)-acetic acid ethyl ester 49

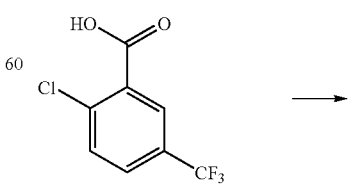

46

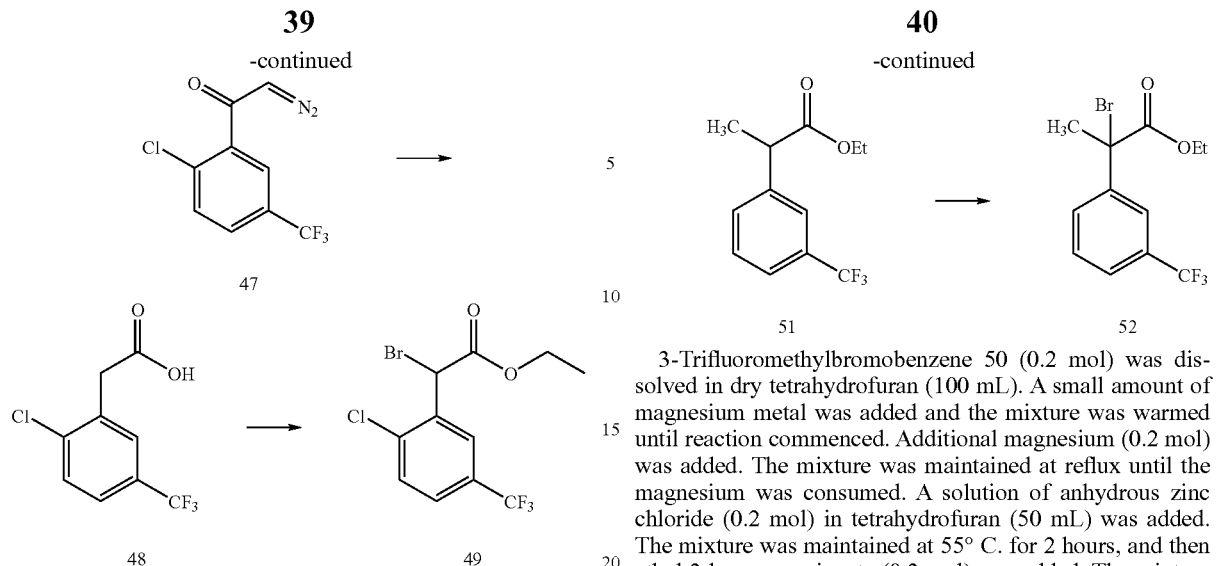

2-Chloro-5-trifluoromethyl benzoic acid 46 (0.1 mol) was dissolved in dichloromethane (100 mL). To which was then added thionyl chloride (0.2 mol) and dimethylformamide (0.1 mL). After 1 hour the solvents were removed under vacuum. The residue was dissolved in ethyl acetate and ethereal diazomethane (0.2 mol) was added. After 1 hour the solvents were removed under reduced pressure to afford the diazo ketone 47. This compound (0.05 mol) was dissolved in ethanol (100 mL). The solution was brought to reflux and a solution of silver benzoate (0.02 mol) in triethylamine (5 mL) was added. After 10 minutes the solution was cooled, filtered and the filtrate was concentrated to afford a residue. The residue was chromatographed to obtain (2-chloro-5-trifluoromethyl-phenyl)-acetic acid. The above compound (0.02 mol) was dissolved in methanol (20 mL) and a solution of lithium hydroxide monohydrate (0.02 mol) in water (20 mL) was added. The progress of the reaction was monitored by TLC. When it was complete, the mixture was acidified with dilute hydrochloric acid, and extracted with ether. The extract was dried and concentrated to afford (2-chloro-5-trifluoromethyl-phenyl)-acetic acid 48.

Using the above procedure, different benzoic acids can be converted into the corresponding phenylacetic acids.

The acid 48 (0.01 mol) was dissolved in 1,2-dichloroethane (50 mL). Thionyl chloride (0.011 mol) was added, and the mixture was heated at 55° C. for 1 hour. Bromine (0.01 mol) was added. After another 18 hours, the mixture was cooled to 0° C. and ethanol (50 mL) was added. After 2 hours the mixture was added to water and extracted with ether. The extract was dried and concentrated to afford the title compound, 49.

Using the above procedure, different phenylacetic acids can be transformed into the corresponding bromo esters analogous to 49.

Preparation 2.
2-Bromo-2-(3-trifluoromethyl-phenyl)-propionic acid ethyl ester, 52

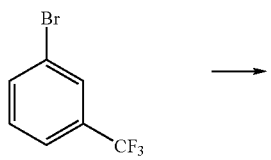

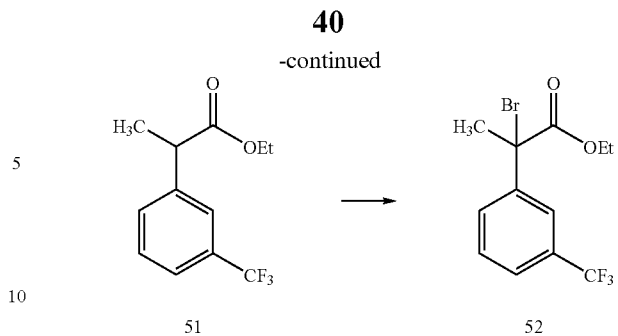

3-Trifluoromethylbromobenzene 50 (0.2 mol) was dissolved in dry tetrahydrofuran (100 mL). A small amount of magnesium metal was added and the mixture was warmed until reaction commenced. Additional magnesium (0.2 mol) was added. The mixture was maintained at reflux until the magnesium was consumed. A solution of anhydrous zinc chloride (0.2 mol) in tetrahydrofuran (50 mL) was added. The mixture was maintained at 55° C. for 2 hours, and then ethyl 2-bromopropionate (0.2 mol) was added. The mixture was maintained at 55° C. and the progress of the reaction was monitored by TLC. When the reaction was complete, the mixture was cooled and added to water and ether. The organic layer was dried and concentrated, and the residue was chromatographed to afford 2-(3-trifluoromethyl-phenyl)-propionic acid ethyl ester 51.

Using the above procedure, but employing differently substituted bromo trifluoromethyl benzenes in place of 50, and different bromoesters in place of ethyl 2-bromopropionate, the corresponding compounds analogous to 51 were obtained.

The ester 51 (0.05 mol) was dissolved in carbon tetrachloride (75 mL) and N-bromosuccinimide (0.05 mol) was added. The mixture was heated at reflux and the progress of the reaction was monitored by TLC. When the reaction was complete, the mixture was cooled and filtered. The solution was concentrated to afford the title compound 52.

Using the above procedure, but employing different esters in place of 51, prepared as described above, different bromo esters analogous to 52 were obtained.

Preparation 3.
Bromo-(4-trifluoromethyl-phenyl)-acetic acid methyl ester, 56

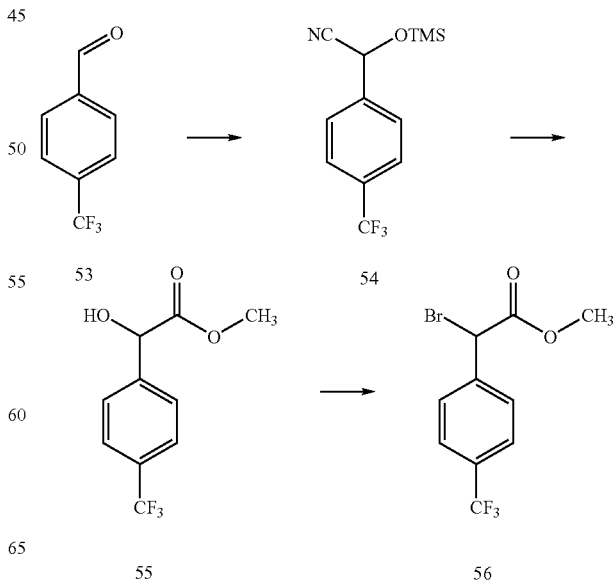

4-Trifluoromethylbenzaldehyde 53 (0.1 mol) was dissolved in dichloromethane (150 mL) and a catalytic amount of potassium cyanide and 18-Crown-6 were added. The mixture was cooled in ice and trimethylsilyl cyanide (0.1 mol) was added. After 16 hours at 25° C. the solution was washed with aqueous sodium bicarbonate, dried and concentrated, to afford the silyl cyanohydrin 54. This material was dissolved in methanol (100 mL) and hydrogen chloride was bubbled into the solution for several minutes at 0° C. After 16 hours at 25° C., the mixture was neutralized with aqueous sodium hydroxide and extracted with ethyl acetate. The extract was dried and concentrated, and the residue was chromatographed to afford hydroxy-(4-trifluoromethyl-phenyl)-acetic acid methyl ester, 55.

Using the above procedures, differently substituted trifluoromethyl benzaldehydes were converted into the corresponding hydroxy esters.

The ester 55 (0.05 mol) and triphenylphosphine (0.05 mol) were dissolved in dichloromethane (250 mL) at 0° C. and carbon tetrabromide (0.05 mol) was added. After 16 hours at 25° C., the solvent was removed and 2:3 hexane:ethyl acetate (300 mL) were added. A precipitate was removed by filtration and the solvent was removed under vacuum. The residue was chromatographed to afford the title compound 56.

Using the above procedure, different hydroxyesters, prepared as described in B above, can be converted into the corresponding bromoesters.

Preparation 4. 2,4-Bis-trifluoromethyl-benzenethiol, 60

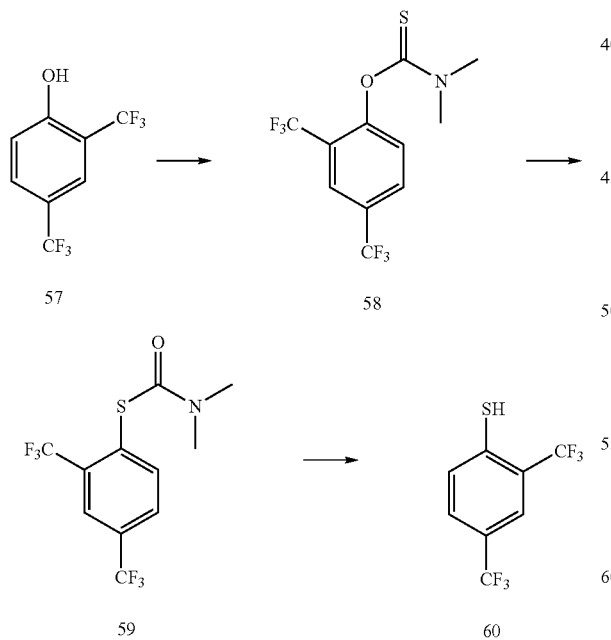

2,4-Di(trifluoromethyl)phenol 57 (0.1 mol) was dissolved in pyridine (50 mL) and dimethylaminothiocarbamoyl chloride (0.1 mol) was added. The mixture was heated at 600 for 12 hours, then was cooled and added to water. The aqueous solution was extracted with ether, and the extract was washed with dilute hydrochloric acid, then dried and concentrated to afford dimethyl-thiocarbamic acid O-(2,4-bis-trifluoromethyl-phenyl) ester 58. This compound was dissolved in N-methyl pyrrolidinone (50 mL) and the solution was heated at reflux. The progress of the reaction was monitored by TLC. When it was complete, the cooled solution was added to water and extracted with ether. The extract was dried and concentrated and the residue was chromatographed to afford dimethyl-thiocarbamic acid S-(2,4-bis-trifluoromethyl-phenyl)ester 59. This compound (0.05 mol) was dissolved in methanol, and 1N aqueous sodium hydroxide (0.05 mol) was added. The progress of the reaction was monitored by TLC. When it was complete, the solution was added to dilute hydrochloric acid and extracted with ether. The extract was dried and concentrated to afford the title compound 60.

Using the above procedures, but employing different trifluoromethyl substituted phenols, the corresponding thiophenols were obtained.

Preparation 5.
Mercapto-(4-trifluoromethyl-phenyl)-acetic acid methyl ester 63

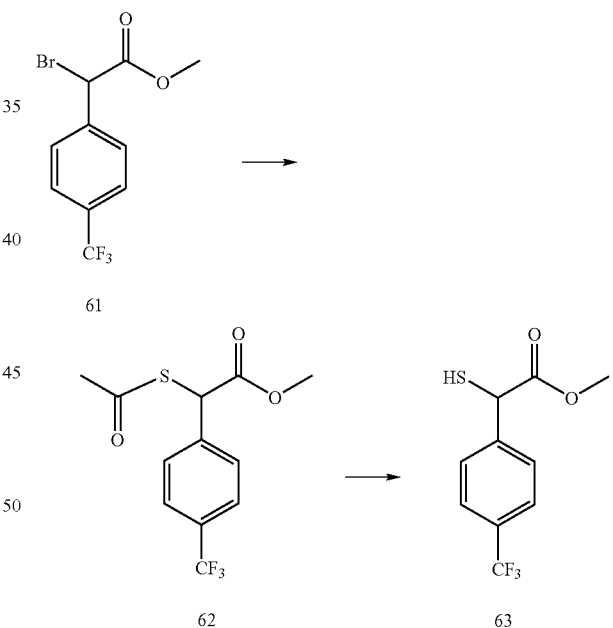

Bromo-(4-trifluoromethyl-phenyl)-acetic acid methyl ester 61 (0.05 mol) was dissolved in tetrahydrofuran (25 mL) and a solution of sodium thiolacetate (0.05 mol) in water (5 mL) was added. The progress of the reaction was monitored by TLC. When it was complete, the solution was added to dilute hydrochloric acid and extracted with ether. The extract was dried and concentrated to provide compound 62. The residue 62 was dissolved in methanol and 5% aqueous ammonia (10 mL) was added. After 2 hours, the mixture was acidified with dilute hydrochloric acid and extracted with ether. The organic phase was dried and concentrated and the residue was chromatographed to afford the title compound 63.

Using the above procedure, but employing different bromoesters, the corresponding mercapto esters can be obtained.

Preparation 6.
2,5-Bis-trifluoromethyl-benzaldehyde, 66

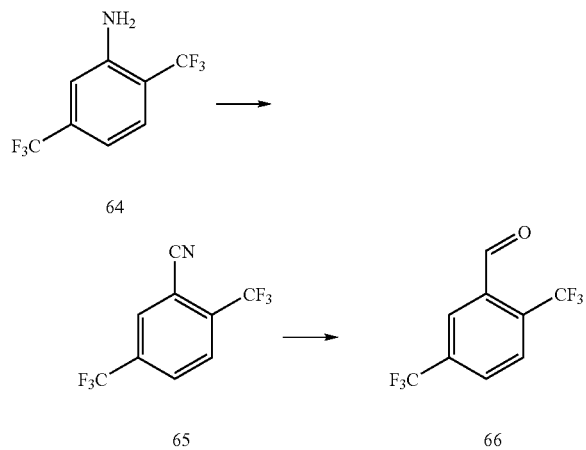

2,5-Di(trifluoromethyl)aniline 64 (0.1 mol) was dissolved in concentrated hydrochloric acid (20 mL) and water (150 mL). The solution was cooled to 0° C. and a solution of sodium nitrite (0.1 mol) in water (50 mL) was added with vigorous stirring. After 10 minutes, the above solution was added to a solution of nickel cyanide (0.1 mol) in water (100 mL) at 0° C. After 2 hours, the mixture was heated to 60° C. for 30 minutes, then cooled and extracted with ethyl acetate. The extract was dried and concentrated, and the residue was chromatographed to afford 2,5-bis-trifluoromethylbenzonitrile 65. This compound (0.05 mol) was dissolved in toluene (50 mL). The solution was cooled to −80° C. and a 1.5M solution of diisobutylaluminum hydride (0.05 mol) in toluene was added. After 2 hours, the mixture was warmed to 50° C. for 1 hour. Water was added, and the organic phase was dried and concentrated. The residue was chromatographed to afford the title compound 66.

Using the above procedures, different trifluoromethyl-substituted anilines can be converted into the corresponding benzaldehydes.

Preparation 7. 2-Trifluoromethyl-4-nitrophenol 69 and 2-trifluoromethyl-4-trifluoromethyl acetamino-phenol 71

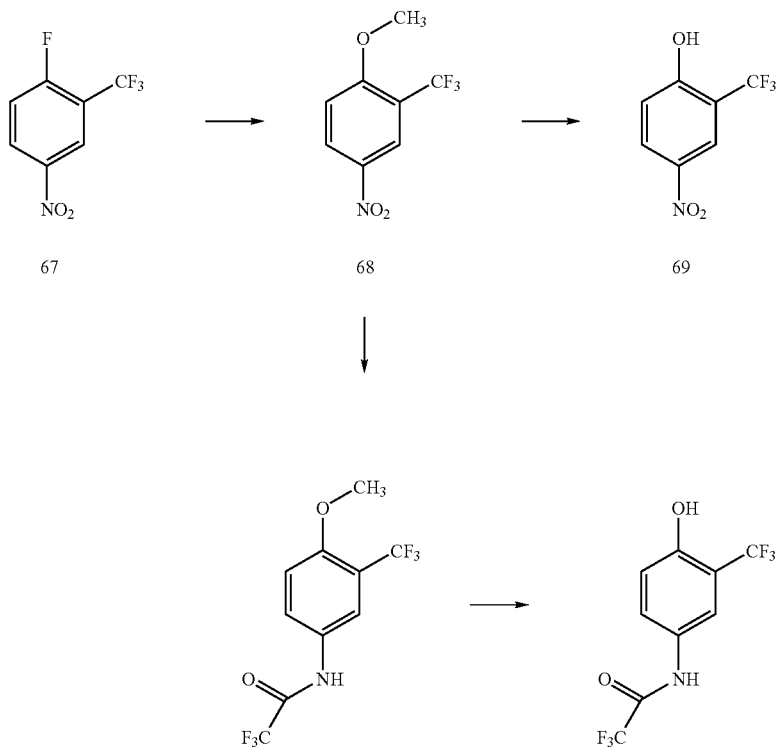

1-Fluoro-4-nitro-2-trifluoromethylbenzene 67 (0.1 mol), was dissolved in tetrahydrofuran (100 mL). The solution was cooled to 0° C. and sodium methoxide (0.1 mol) was added. The reaction was warmed to room temperature over 2 hours. Water and ethyl acetate were added. The organic phase was dried and concentrated to afford 1-methoxy-4-nitro-2-trifluoromethylbenzene 68. This material was dissolved in methylene chloride (100 mL) and the solution was cooled to −78° C. Boron tribromide (0.1 mol) was added. The mixture was warmed to room temperature. Water was added, and the organic phase was dried and concentrated. Chromatography then afforded the title compound 69.

1-Methoxy-4-nitro-2-trifluoromethylbenzene 68 (0.1 mol) and $SnCl_2$ (1 mol) was mixed in EtOAc. The mixture was stirred at rt for 2 hrs and then refluxed for 3 hrs until TLC indicated the completion of the reaction. The reaction mixture was cooled and quenched with aqueous $NaHCO_3$. The solid was filtered through a celite pad and washed with EtOAc. The organic layer of the filtrate was collected, dried and concentrated to afford the corresponding aniline. To the aniline (0.05 mol) in methylene chloride (200 mL) was added $Et_3N$ and $(CF_3CO)_2O$ at 0° C. The reaction was allowed to warm to 25° C. with stirring. The reaction was then worked up between EtOAc and water. The organic layer was dried and concentrated. The residue was purified on silica gel column to afford 70. This material is dissolved in methylene chloride (100 mL) and the solution was cooled to −78° C. Boron tribromide (0.1 mol) was added. The mixture was warmed to room temperature. Water was added, and the organic phase was dried and concentrated. Chromatography afforded the title compound 71.

Using the above procedures, but employing differently substituted fluorobenzenes, the correspondingly substituted phenols were obtained.

Preparation 8. (2-Acetamidoethyl)-4-trifluoromethylphenylbromoacetate 73

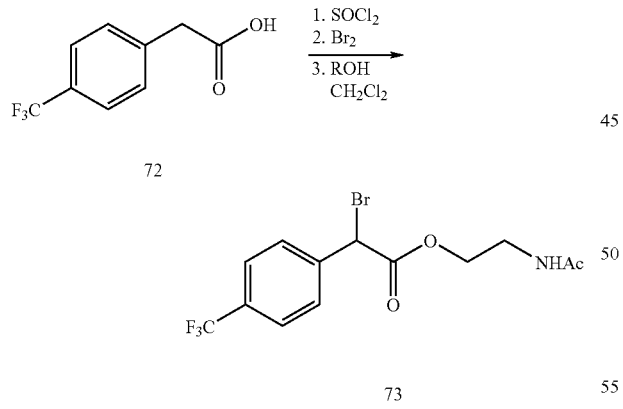

A 250 mL three neck roundbottom flask was equipped with an efficient condenser attached to an acid scrubber, a magnetic stir bar, and placed under argon. 4-Trifluoromethylphenyl acetic acid 72 (0.25 mole) was charged, followed by thionyl chloride (0.34 mole). The condenser was cooled with 4° C. water. The mixture was heated to an internal temperature of 55-60° C. Gas evolution was observed and the solids dissolved as the internal temperature rose to 55-60° C. The mixture was then stirred at 55-60° C. for 45 min. Bromine (33.0 mL, 0.33 mole) was charged and the mixture was maintained at 55-60° C. for 18 h. The internal temperature was then raised to 80-85° C. over 1.5 h and heating continued for 18 h. The mixture was cooled to 20-25° C. and anhydrous dichloromethane (250 mL) was added. In a separate flask was placed 2-acetylethanolamine (1.03 mole) and anhydrous dichloromethane (250 mL) under argon and the mixture cooled to 2-8° C. To this was added the acyl halide solution at such a rate as to keep the internal temperature below 21° C. After the addition was complete, the mixture was stirred for 0.5 h. This mixture was carefully added to water (0.75 L) containing sodium bicarbonate (0.9 mole) at such a rate that frothing was moderate. Sodium thiosulfate (0.06 mole) was added in portions and gas evolution was observed. The layers were then partitioned in a separatory funnel (100 mL dichloromethane used in transfer), and the organic phase was extracted with 125 mL of water, dried over magnesium sulfate (10 g), and filtered. The filter cake was washed with dichloromethane (150 mL). Rotary evaporation and pumping at high vacuum afforded an oil, which was slurried in 100 mL hexane: ethyl acetate (70:30). Additional hexane (150 mL) was added until a white color formed in the top layer of the biphasic mixture. Vigorous agitation afforded a solid, which was filtered away from the supernatant to yield (2-acetamidoethyl)-4-trifluoromethylphenylbromoacetate.

Using the above procedure, but employing differently substituted phenylacetic acids, the corresponding cc-bromophenylacetates were obtained.

Preparation 9. 5-Trifluoromethyl-2-(3-trifluoromethyl-phenoxy)-phenylamine 77

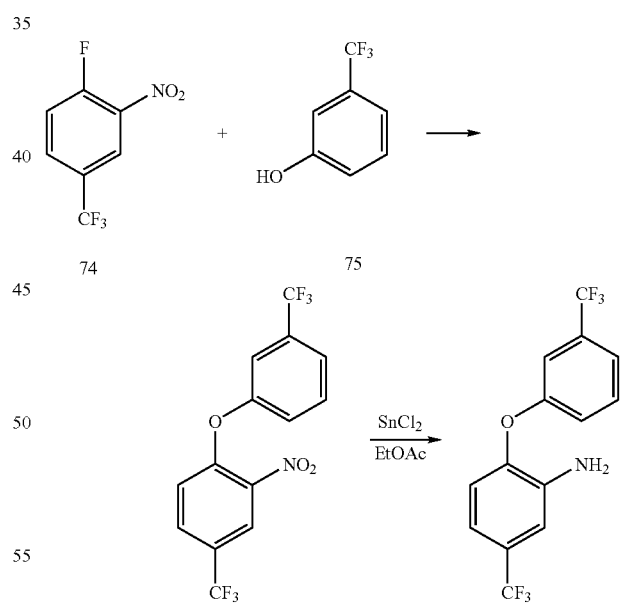

Phenol 75 (0.5 mol) was stirred at 25° C. with $K_2CO_3$ in DMF for 2 hrs. The mixture was then cooled to 0° C., to which was then added 74 in DMF slowly. The reaction mixture was stirred and allowed to warm to 25° C. The reaction was worked up between water and EtOAc after TLC indicated the completion of the reaction. The organic layer was dried and concentrated to afford compound 76.

A mixture of compound 76 (100 g) and and SnCl$_2$.H$_2$O (321 g) in EtOAc (1000 mL) was stirred at room temperature overnight. The reaction mixture was basified by adding aqueous KOH solution. The organic layer was washed with brine, dried and concentrated to give compound 77 as a pale yellow oil, which was used for next reaction without purification. $^1$H NMR (CDCl$_3$, 400 MHz) δ 7.49-6.90 (m,7H), 4.06 (s, 2H).

Using the above procedure, but employing differently substituted nitrofluorobenzene and phenols, the corresponding anilines were obtained.

Preparation 10.
α-Bromo-(3-trifluoromethyl-phenyl)-acetic acid ethyl ester, 79

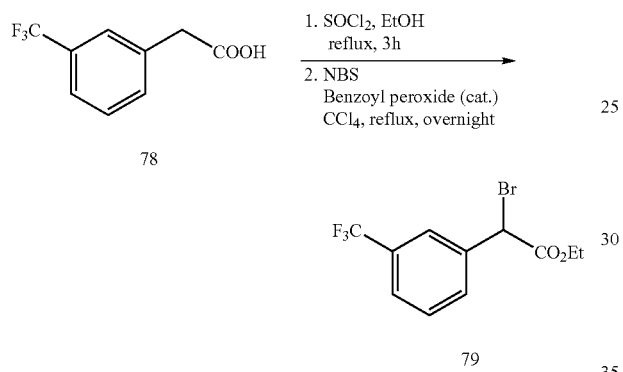

To a solution of (α,α,α-trifluoro-m-tolyl)acetic acid 78 (202.36 g, 0.99 mol) in absolute ethanol (1.0 L) at 0° C. was added thionyl chloride (79 mL, 1.05 mol), and then the resulting solution was refluxed for 3 h. Concentration in vacuo gave a residue which was partitioned between EtOAc and water. The organic layer was washed with sat. NaHCO$_3$ and brine, dried over Na$_2$SO$_4$ and concentrated in vacuo to afford 220.1 g of ethyl ester as a pale yellow liquid.

To a mixture of crude ethyl ester (119.15 g, 0.51 mol) and NBS (100.48 g, 0.56 mol) in CCl$_4$ (1.0 L) was added benzoyl peroxide (1.0 g). The resulting mixture was heated at 75° C. for 20 min. and then refluxed at 90° C. overnight (14 h) until the brown mixture was turned to a pale-color with white precipitate. The mixture was cooled to 0° C., filtered through a pad of celite, concentrated in vacuo to afford 151.27 g (95%) of bromide 79 as a pale brown liquid. This product was sufficiently pure to be used directly in subsequent substitute reaction. This product was also prepared by refluxing (α,α,α-trifluoro-m-tolyl)acetic acid 78 with bromine in the presence of SOCl$_2$, and then quenching with EtOH. $^1$H NMR (400 MHz, CDCl$_3$): δ 7.80 (1H, s), 7.77 (1H, d), 7.61 (1H, d,), 7.51 (1H, t), 5.35 (1H, s), 4.26 (2H, q), 1.30 (3H, t) ppm.

Using the above procedure, but employing differently substituted phenylacetic acids, corresponding α-bromo-phenylacetates are obtained.

Example 1

Preparation of (4-Trifluoromethyl-phenoxy)-(3-trifluoromethyl-phenyl)-acetic acid 39

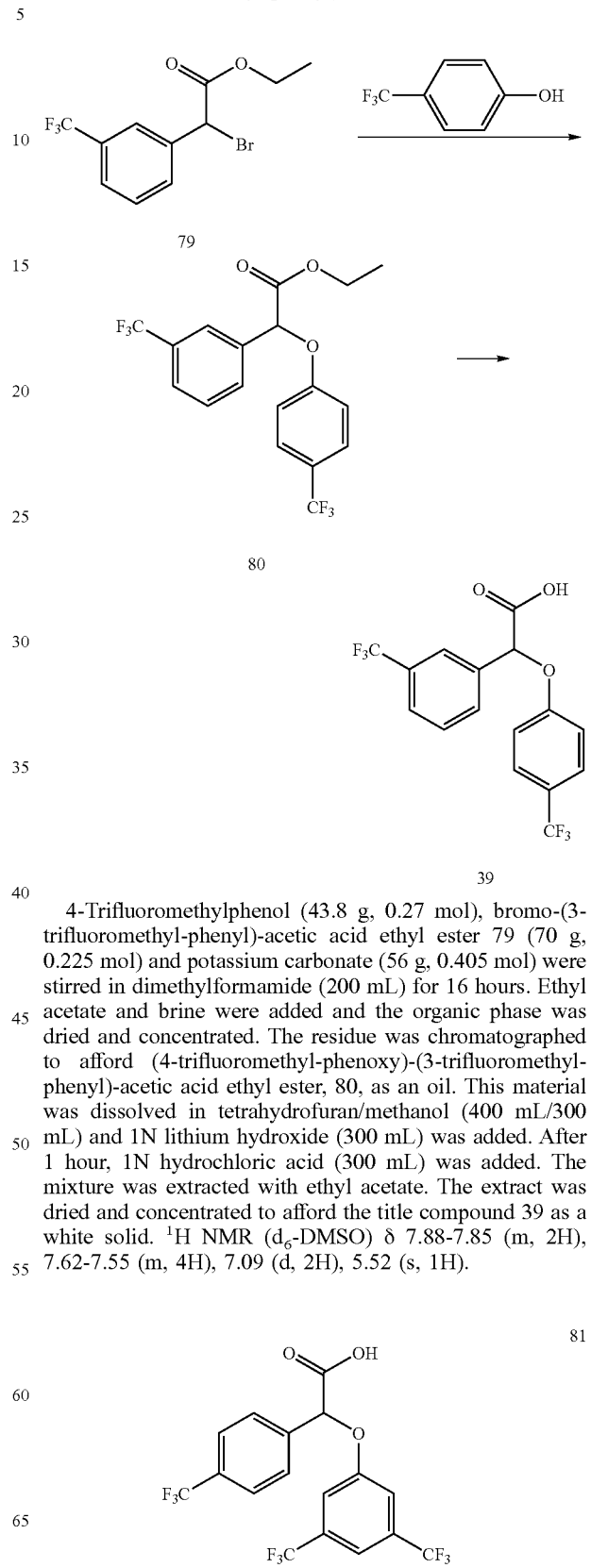

4-Trifluoromethylphenol (43.8 g, 0.27 mol), bromo-(3-trifluoromethyl-phenyl)-acetic acid ethyl ester 79 (70 g, 0.225 mol) and potassium carbonate (56 g, 0.405 mol) were stirred in dimethylformamide (200 mL) for 16 hours. Ethyl acetate and brine were added and the organic phase was dried and concentrated. The residue was chromatographed to afford (4-trifluoromethyl-phenoxy)-(3-trifluoromethyl-phenyl)-acetic acid ethyl ester, 80, as an oil. This material was dissolved in tetrahydrofuran/methanol (400 mL/300 mL) and 1N lithium hydroxide (300 mL) was added. After 1 hour, 1N hydrochloric acid (300 mL) was added. The mixture was extracted with ethyl acetate. The extract was dried and concentrated to afford the title compound 39 as a white solid. $^1$H NMR (d$_6$-DMSO) δ 7.88-7.85 (m, 2H), 7.62-7.55 (m, 4H), 7.09 (d, 2H), 5.52 (s, 1H).

-continued

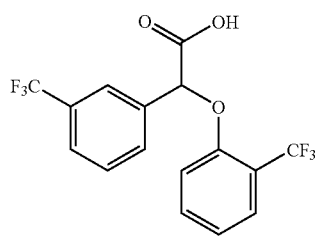
82

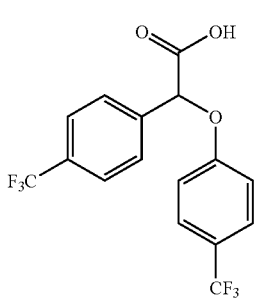
83

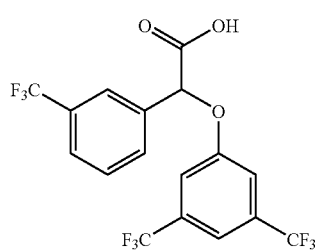
84

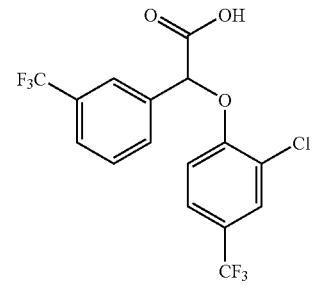
85

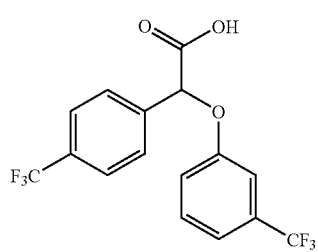
86

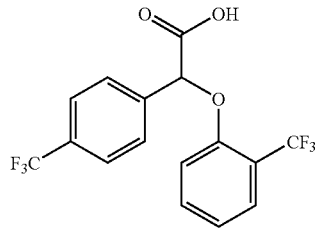
87

-continued

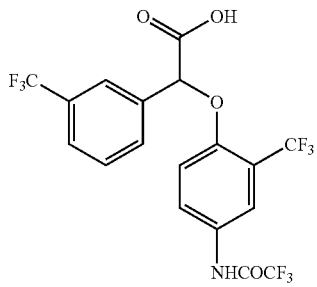
88

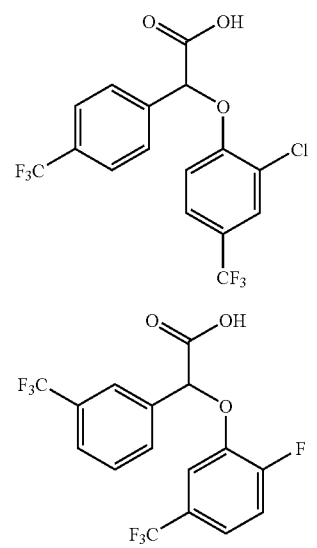
89

90

Using the above procedures, but substituting the appropriate phenols and bromoesters for 79, the following compounds were obtained: (2-Trifluoromethyl-phenoxy)-(3-trifluoromethyl-phenyl)-acetic acid, 82, $^1$H NMR (400 MHz, DMSO-$d_6$): δ 7.94 (1H, s), 7.85 (1H, d), 7.72 (1H, d), 7.65 (1H, d), 7.64 (1H, d), 7.59 (1H, t), 7.14 (1H, d), 7.10 (1H, t), 6.01 (1H, s) ppm; (4-Trifluoromethyl-phenoxy)-(4-trifluoromethyl-phenyl)-acetic acid, 83, $^1$H-NMR (400 MHz, DMSO-$d_6$): δ 7.80-7.15 (m, 8H), 6.16 (s, 1H); (3,5-Bis-trifluoromethyl-phenoxy)-(3-trifluoromethyl-phenyl)-acetic acid, 84, $^1$H-NMR (400 MHz, DMSO-$d_6$): δ 13.80 (s, 1H), 7.94 (s, 1H), 7.88 (d, 1H), 7.78 (d, 1H), 7.73-7.69 (m, 4H), 6.49 (s, 1H); (2-Chloro-4-trifluoromethyl-phenoxy)-(3-trifluoromethyl-phenyl)-acetic acid, 85, $^1$H-NMR (400 MHz, DMSO-$d_6$) δ 9.60 (s, 1H), 7.91 (s, 1H), 7.84 (d, 1H), 7.68-7.66 (m, 2H), 7.58-7.54 (m, 1H), 7.44-7.42 (m, 1H), 6.91 (d, 1H), 5.79 (s, 1H); (3-trifluoromethyl-phenoxy)-(4-trifluoromethyl-phenyl)-acetic acid, 86, $^1$H-NMR (400 MHz, DMSO-$d_6$): δ 7.80-7.30 (m, 8H), 6.25 (s 1H); (2-trifluoromethyl-phenoxy)-(4-trifluoromethyl-phenyl)-acetic acid, 87, $^1$H-NMR (400 MHz, DMSO-$d_6$): δ 7.90-7.20 (m, 8H), 6.28 (s, 1H); [2-trifluoromethyl-4-(2,2,2-trifluoro-acetylamino)-phenoxy]-(3-trifluoromethyl-phenyl)-acetic acid, 88, $^1$H-NMR (400 MHz, DMSO-$d_6$) δ 11.40 (s, 1H), 7.98 (d, 1H), 7.92-7.85 (m, 3H), 7.77 (d, 1H), 7.72 (m, 1H), 7.25 (d, 1H), 6.30 (s, 1H); (2-Chloro-4-trifluoromethyl-phenoxy)-(4-trifluoromethyl-phenyl)-acetic acid, 89, $^1$H-NMR (400 MHz, DMSO-$d_6$) δ 7.88-7.80 (m, 5H), 7.71 (dd, 1H), 7.28 (d, 1H), 6.34 (s, 1H); and (2-Fluoro-5-trifluoromethyl-phenoxy)-(4-trifluoromethyl-phenyl)-acetic acid, 90, $^1$H-NMR (CDCl$_3$, 400 MHz) δ 7.85 (s, 1H), 7.80 (d, 1H), 7.68 (d, 1H), 7.58 (m, 1H), 7.32-7.23 (m, 3H), 5.78 (s, 1H).

Example 2

Preparation of (3-fluoro-5-trifluoromethyl-phenyl)-(5-methoxy-2-trifluoromethyl-phenoxy)-acetic acid, 94

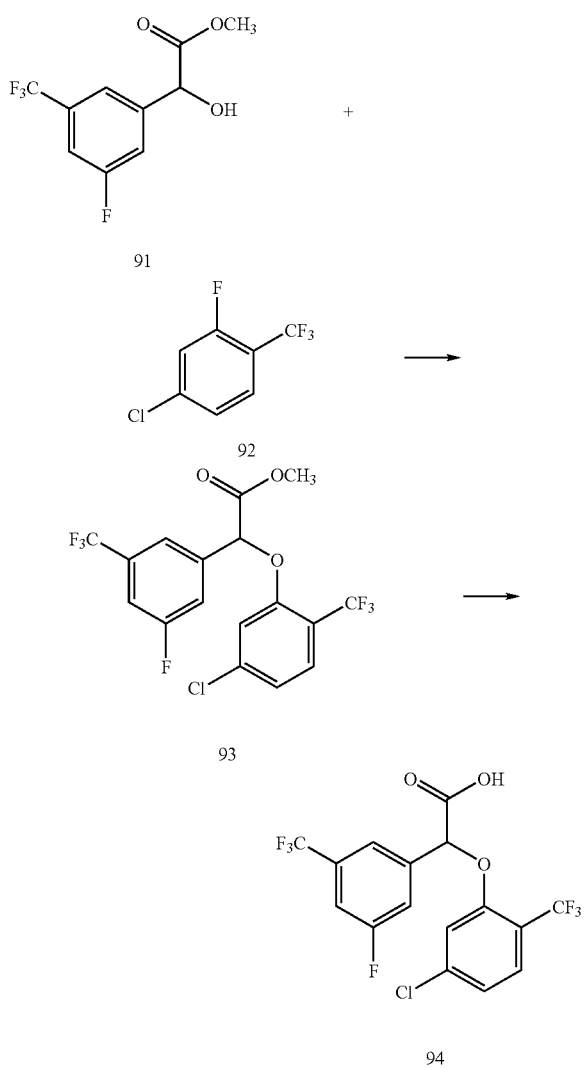

(3-Fluoro-5-trifluoromethyl-phenyl)-hydroxy-acetic acid methyl ester 91 (0.1 mol) was dissolved in dimethylformamide (100 mL) and sodium hydride (0.1 mol) was added. When hydrogen evolution stopped, a solution of 2-fluoro-4-chloro-1-trifluoromethyl-benzene 92 (0.1 mol) in dimethylformamide (25 mL) was added. The progress of the reaction was monitored by TLC. When the reaction was complete, water and ethyl acetate were added. The organic phase was dried and concentrated, and the residue was chromatographed to afford (3-fluoro-5-trifluoromethyl-phenyl)-(5-chloro-2-trifluoromethyl-phenoxy)-acetic acid methyl ester 93. Basic hydrolysis of this compound, as described in Example 1, then afforded the title compound 94.

Using the above procedures, but employing different hydroxy esters and fluorobenzenes, the corresponding compounds analogous to 94 can be obtained.

Example 3

Preparation of (2,4-bis-trifluoromethyl-phenoxy)-(3-trifluoromethyl-phenyl)-acetic acid ethyl ester 97

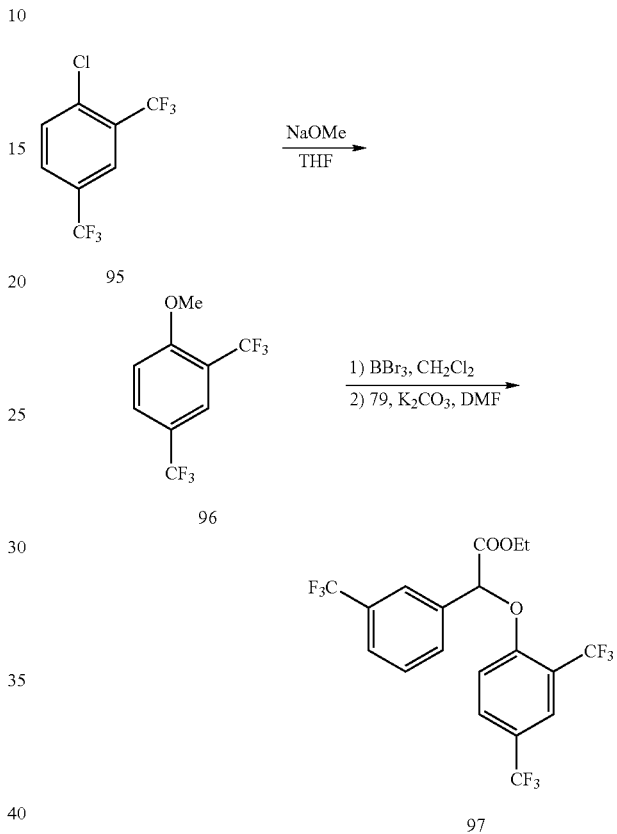

To a solution of 95 (25.0 g, 0.10 mol) in anhy. THF (150 mL) was added NaOCH$_3$ (7.0 g, 0.13 mol) at 0° C. The mixture was then heated at 50° C. for 6 h. After cooling to 25° C., the reaction mixture was quenched with sat. NH$_4$Cl, diluted with EtOAc, washed with brine, and concentrated in vacuo to afford crude methyl ether 96 (17.93 g, 73%) as a colorless liquid. This product was sufficiently pure to be used directly in subsequent reaction. $^1$H NMR (400 MHz, CDCl$_3$): δ 7.83 (1H, s), 7.77 (1H, d, J=8.4 Hz), 7.09 (1H, d, J=8.4 Hz), 3.97 (3H, s) ppm. A solution of methyl ether 96 (9.98 g, 0.04 mol) in anhyrous CH$_2$Cl$_2$ (150 mL) was cooled to −78° C. and treated with BBr$_3$ (6.0 mL, 0.063 mol). The resultant brown mixture was stirred for 1 h at −78° C., and then warmed up to 25° C. over 4 h, and then quenched with water. The organic layer was separated and washed with sat. NaHCO$_3$ and brine, dried over Na$_2$SO$_4$, concentrated to ~13 mL in vacuo below 0° C. and used directly in the following substitution reaction. Take this solution (ca. 1.15 mL) and diluted with DMF (8 mL), and then treated with K$_2$CO$_3$ (1.27 g) and bromide 79 (1.72 g). The resultant mixture was stirred at room temperature for 1 h, diluted with EtOAc, washed with water and brine, dried over Na$_2$SO$_4$, and concentrated in vacuo. The residue was purified by flash chromatography (5:95 EtOAc/hexanes) on silica gel and then recrystallized with 10% EtOAc/hexanes to give pure ester 97 as a white solid. $^1$H NMR (400 MHz, DMSO-$d_6$): δ 8.60 (1H, d, J=2.2 Hz), 8.17 (1H, dd, J=8.6, 2.2 Hz), 7.96 (1H, s), 7.91 (1H, d, J=8.6 Hz), 7.84 (1H, d, J=8.2 Hz), 7.74 (1H, t, J=7.8 Hz), 7.38 (1H, d, J=9.0 Hz), 6.40 (1H, s), 4.19 (2H, m), 1.11 (3H, t, J=7.2 Hz) ppm.

Example 4

Preparation of (3-trifluoromethyl-phenyl)-(5-trifluoromethyl-pyridin-2-yloxy)-acetic acid, 100

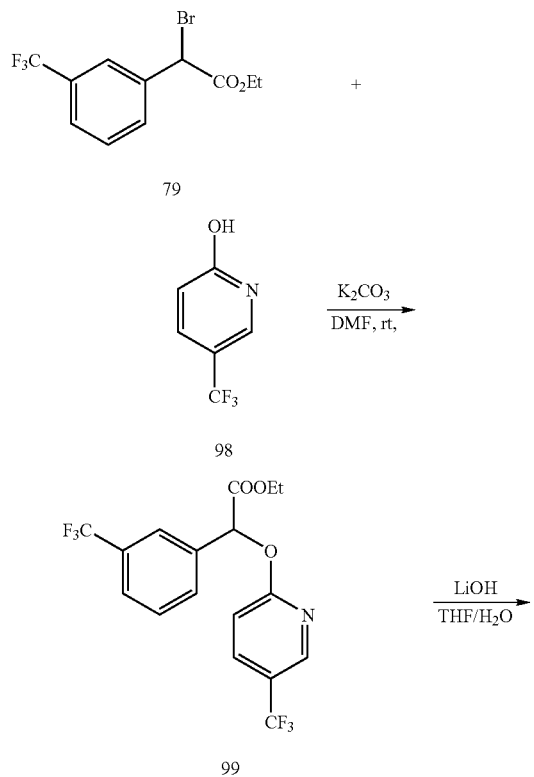

-continued

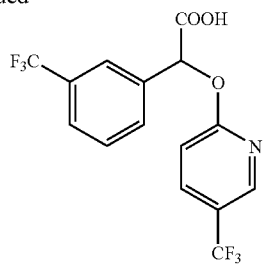

100

To a solution of 5-(trifluoromethyl)-2-pyridinol 98 (2.11 g, 12.9 mmol) in DMF (20 mL) was added K$_2$CO$_3$ (2.68 g, 19.4 mmol) followed by bromide 79 (4.68 g, 15.0 mol). The resulting mixture was stirred at room temperature overnight, diluted with EtOAc, and washed with water. The organic layer was washed with sat. NaHCO$_3$ and brine, dried over Na$_2$SO$_4$, concentrated in vacuo, and purified by flash chromatography on silica gel (5:95 EtOAc/hexanes) to afford ester 99 (0.61 g, 12%) as a pale-yellow liquid. To a solution of ester 99 (0.61 g, 1.55 mmol) in THF/H$_2$O (10 mL/3 mL) at room temperature was added lithium hydroxide monohydrate (0.31 g, 7.39 mmol). The resulting solution was stirred at room temperature for 2 h. The reaction was quenched with 1N aqueous HCl and the mixture was extracted with EtOAc. The organic layer was washed with brine, dried over Na$_2$SO$_4$ and concentrated in vacuo to afford acid 100 (0.53 g, 94%) as a brown liquid. $^1$H NMR (400 MHz, DMSO-$d_6$): δ 8.55 (1H, s), 8.08 (1H, dd, J=8.8, 2.6 Hz), 7.89 (1H, s), 7.86 (1H, d, J=8.0 Hz), 7.71 (1H, d, J=8.0 Hz), 7.61 (1H, d, J=7.6 Hz), 7.14 (1H, d, J=8.0 Hz), 6.19 (1H, s) ppm.

Using the above procedures, but employing different bromo-phenylacetic esters and pyridinols, compounds analogous to 100 can be obtained.

Example 5

Preparation of 2-(4-trifluoromethyl-phenyl)-3-(3-trifluoromethyl-phenyl)-propenoic acid, 104 and 2-(4-trifluoromethyl-phenyl)-3-(3-trifluoromethyl-phenyl)-propionic acid 105

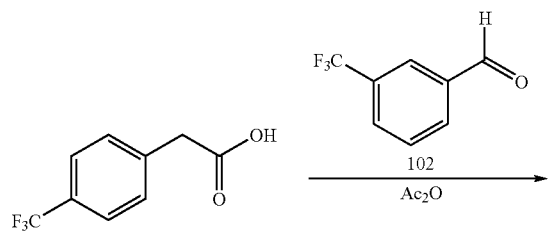

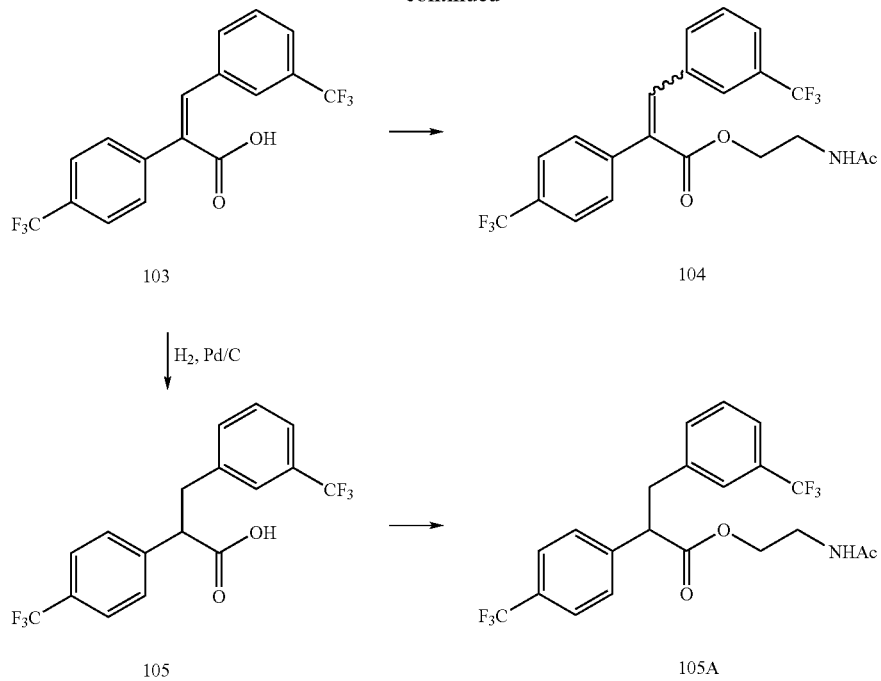

A one neck roundbotton flask was equipped with a Claisen adapter, temperature probe, water condenser, and nitrogen line. The apparatus was flushed with nitrogen. The system was charged with potassium acetate (1.52 g, 15.5 mmol), acetic anhydride (69 mL), (α,α,α-trifluoro-p-tolyl) acetic acid (2.97 g, 14.5 mmol), and α,α,α-trifluoro-m-tolualdehyde (2 mL, 2.6 g, 14.9 mmole) with stirring. As the solution was heated, all solid dissolved around 75° C. and the solution became clear yellow. The mixture was heated to 106° C. for 18.5 hours. The heat was removed and the reaction conversion checked by TLC. Deionized water (16 mL) was added to the reaction flask at a rate such that the solution temperature was maintained at 70-80° C. An additional 20 mL of deionized water was added after the solution had cooled to ambient temperature and this caused crystals to start to precipitate. Finally, an additional 20 mL deionized water was added and the solution was allowed to stir overnight at room temperature. The solution was vacuum filtered at room temperature and the crystals were washed twice with 20 mL deionized water. The crystals were dried under high vacuum to afford a beige powder of cis-3-(3-trifluoromethylphenyl)-2-(4-trifluoromethylphenyl)-propenoic acid (3.542 g, 9.8 mmol) 104.

A one neck, 100 mL round bottom flask equipped with addition funnel (filled with 3 Å molecular sieves), water condenser, oil bath, and nitrogen line was charged with Z-3-(3-trifluoromethylphenyl)-2-(4-trifluoromethylphenyl)-acrylic acid (1.2 g, 3.33 mmol), N-acetylethanolamine (7 mL), dry dimethoxyethane (36 mL), and concentrated sulfuric acid (0.05 mL). The reaction mixture was heated to reflux for 16.5 hours. After the solution was cooled to room temperature, it was partitioned between 100 mL ethyl acetate and 100 mL water. The layers were separated and the organic layer was washed with aqueous sodium bicarbonate solution. The organic phase was dried over magnesium sulfate and concentrated by rotovap and high vacuum, yielding 1.55 g of a viscous brown oil. The product was purified by flash chromatography using a solvent system consisting of 5% acetic acid in chloroform. The fractions containing product were combined and washed with water (2×100 mL) saturated sodium bicarbonate solution (100 mL), dried over magnesium sulfate, and concentrated by rotovap to yield 2-acetamidoethanol-Z-3-(3-trifluoromethylphenyl)-2-(4-trifluoromethylphenyl)-acrylate 104 (855 mg, 1.9 mmol).

The trans adduct was synthesized by isomerizing the cis-carboxylic acid with a sun lamp.

A three neck, one liter round bottom flask equipped with condenser, thermometer, nitrogen line and magnetic stirrer was charged with Z-3-(3-trifluoromethylphenyl)-2-(4-trifluoromethylphenyl)-acrylic acid (103, 2.28 g, 6.3 mmol), ethanol (104 mL), palladium black (101.1 mg) and ammonium formate (1.608 g, 25.5 mmol). The reaction mixture was heated to 80° C. for 4 hours. An aliquot was taken and TLC (solvent system was 20% ethyl acetate in hexanes with an acetic acid spike) showed absence of starting material. The solution was cooled to room temperature and vacuum filtered using a glass frit funnel. The solution was concentrated by rotary evaporation and high vaccum, yielding 3-(3-trifluoromethylphenyl)-2-(4-trifluoromethylphenyl)-propionic acid (2.83 g) 105.

3-(3-Trifluoromethylphenyl)-2-(4-trifluoromethylphenyl)-propionic acid (105, 2.43 g, crude) was dissolved in anhydrous THF (6 mL) at ambient temperature. CDI (1.64 g, 10.1 mmol) was charged as a solid, followed by EtOAc (4 mL), to rinse the vial. The internal temperature remained between 20-21° C. during the addition. N-acetylethanolamine (3.6 mL, 39 mmol) was added, whereupon the temperature rose to 24.5° C. The mixture was stirred overnight (16 h) at 23-24° C. and then rotary evaporated to a gummy residue. This was chromatographed on silica gel using EtOAc: hexane (70:30 v/v) (Rf=0.35-0.40) to afford 2-acetamidoethyl-3-(3-trifluoromethylphenyl)-2-(4-trifluoromethylphenyl)propionate 105A (1.85 g).

Using the above procedures, but employing different phenylacetic esters and benzaldehydes, compounds analogous to 104, 105 and 105A can be obtained.

Example 6

Preparation of (3-Methylsulfanyl-5-trifluoromethyl-phenyl)-(4-nitro-2-trifluoromethyl-phenylsulfanyl)-acetic acid, 109

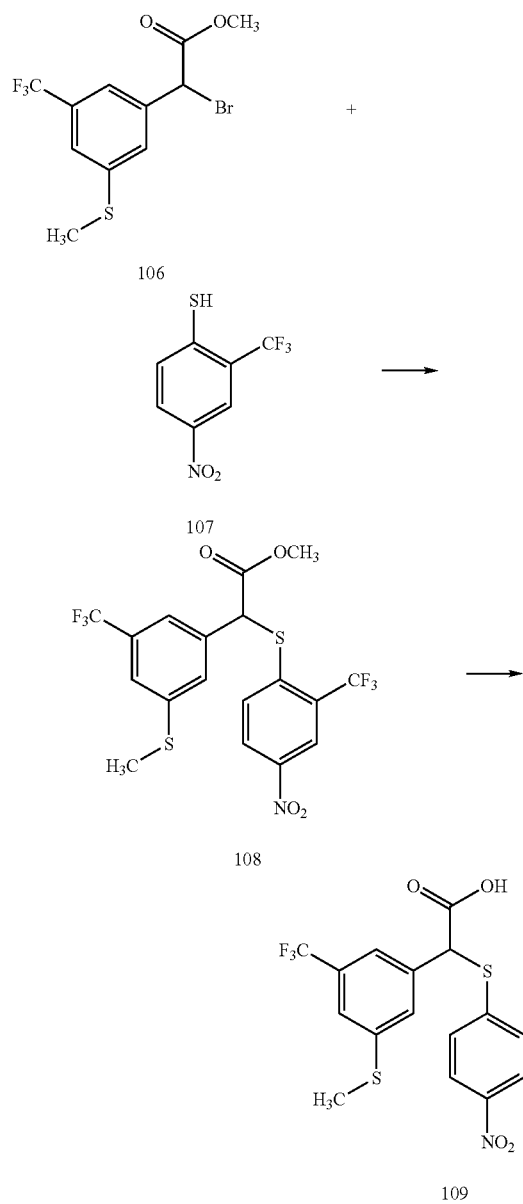

Using the procedures of Example 1, bromo-(3-methylsulfanyl-5-trifluoromethyl-phenyl)-acetic acid methyl ester 106 and 4-nitro-2-trifluoromethyl-benzenethiol 107, prepared as described in Preparation 7 were combined to form (3-methylsulfanyl-5-trifluoromethyl-phenyl)-(4-nitro-2-trifluoromethyl-phenylsulfanyl)-acetic acid methyl ester, 108, which was then hydrolyzed under basic conditions to afford the title compound 109.

Using the above procedure, different bromoesters and thiols can be reacted together to afford the corresponding compounds 1 in which X is S.

Example 7

Preparation of (3-trifluoromethyl-phenyl)-(2-trifluoromethyl-phenylamino)-acetic acid, 112

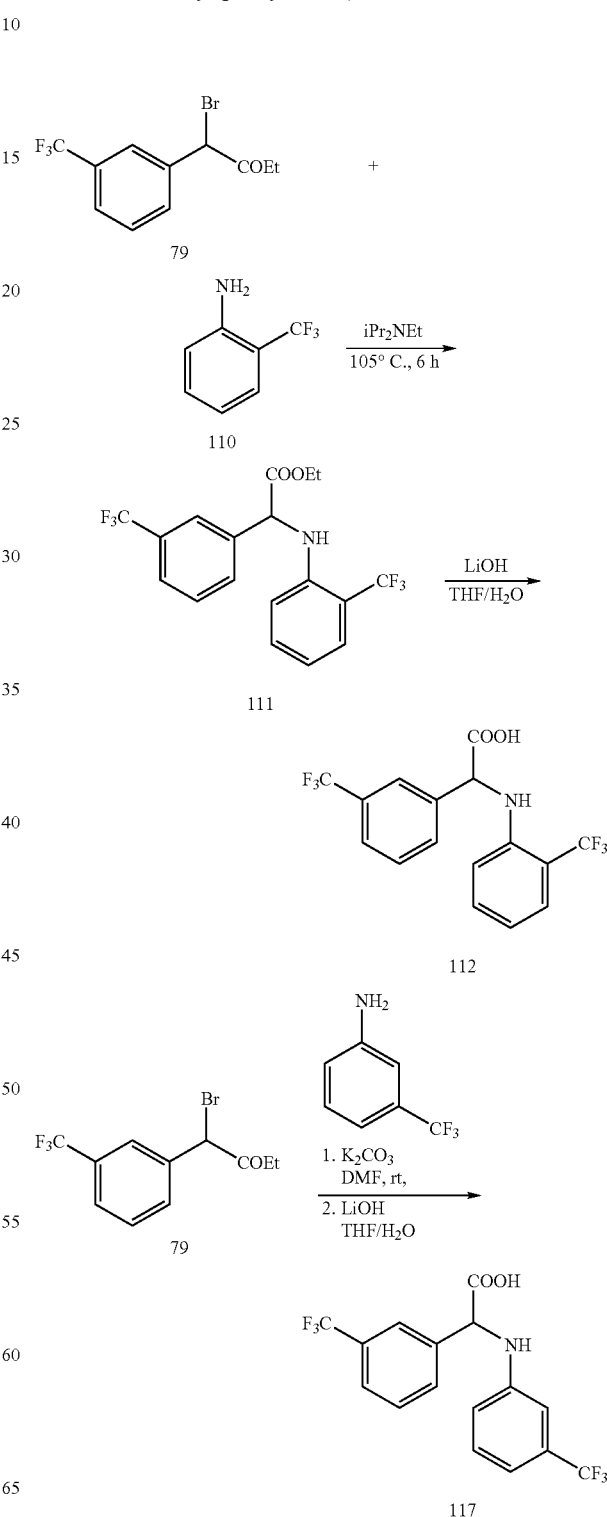

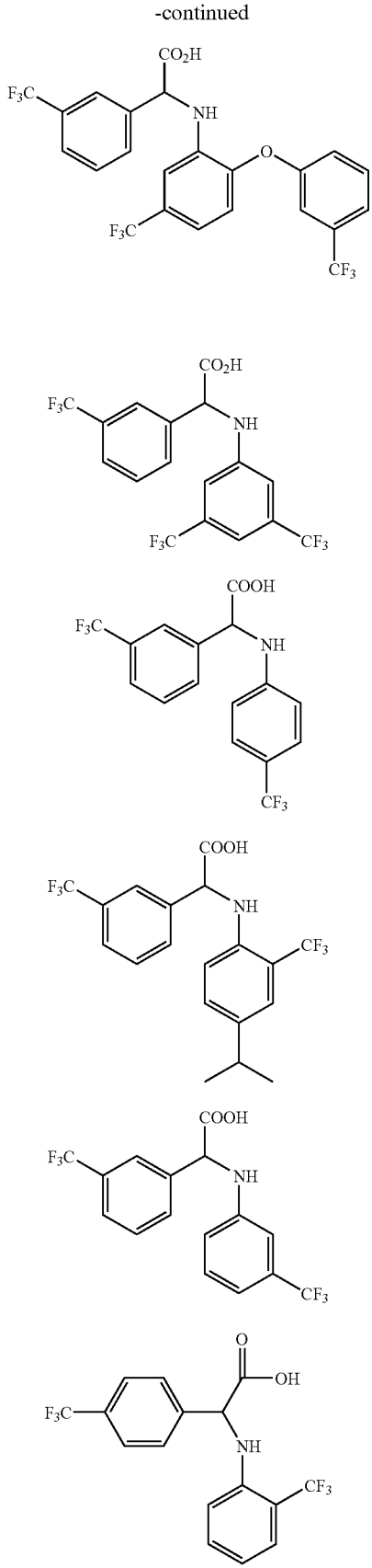

(3-Trifluoromethyl-phenyl)-(2-trifluoromethyl-phenylamino)-acetic acid: A neat mixture of o-trifluoromethylaniline (1.63 g, 10.1 mmol), bromide 79 (1.11 g, 3.57 mmol) and diisopropylethyl amine (1.56 g, 12.1 mmol) was stirred in a capped flask at 105° C. for 6 h. The mixture was cooled to room temperature, diluted with EtOAc, and washed with water. The organic layer was washed with brine, dried over $Na_2SO_4$, concentrated in vacuo, and purified by flash chromatography on silica gel (5:95 EtOAc/hexanes) to afford pure ester 111 (0.19 g, 14%) as a colorless liquid. $^1$H NMR (400 MHz, DMSO-$d_6$): δ 7.86 (1H, s), 7.76 (1H, d), 7.69 (1H, d), 7.63 (1H, t), 7.49 (1H, dd), 7.33 (1H, t), 6.77(1H, t). 6.66 (1H, d), 5.88 (1H, d), 5.73 (1H, d), 4.18 (2H, m), 1.11 (3H, t) ppm. To a solution of ester 111 (0.19 g, 0.49 mmol) in THF/$H_2O$ (4 mL/1.5 mL) at room temperature was added lithium hydroxide monohydrate (0.10 g, 2.38 mmol). The resulting solution was stirred at room temperature for 1 h, quenched with 1N aqueous HCl and extracted with EtOAc. The organic layer was washed with brine, dried over $Na_2SO_4$ and concentrated in vacuo to afford acid 112 (0.13 g, 99%) as an off-white solid. $^1$H NMR (400 MHz, DMSO-$d_6$): δ 13.84 (1H, br, COOH), 7.84 (1H, s), 7.75 (1H, d), 7.68 (1H, d, J=8.0 Hz), 7.62 (1H, t), 7.48 (1H, dd,), 7.30 (1H, t), 6.74 (1H, t), 6.59 (1H, d), 5.96 (1H, d), 5.56 (1H, d) ppm.

(3-Trifluoromethyl-phenyl)-(3-trifluoromethyl-phenylamino)-acetic acid 117: To a solution of 3-trifluoromethylaniline (1.62 g, 0.010 mol) in DMF (30 mL) was added $K_2CO_3$ (2.10 g, 0.015 mol) followed by bromide 79 (3.41 g, 0.011 mol). The resulting mixture was stirred at 55° C. for 3 h. The reaction mixture was cooled to room temperature, diluted with EtOAc, and washed with water. The organic layer was washed with water and brine, dried over $Na_2SO_4$, concentrated in vacuo, and purified by flash chromatography on silica gel (5:95 EtOAc/hexanes) to afford the ester (0.87 g, 22%) as a yellow liquid. $^1$H NMR (400 MHz, DMSO-$d_6$): δ 8.21 (1H, s), 8.14 (1H, d), 8.05 (1H, d), 7.84 (1H, t), 7.65 (1H, d), 7.28 (1H, S), 7.27 (1h, d), 4.16 (2H, m), 0.91 (3H, t) ppm. To a solution of the above ester (0.82 g, 2.10 mmol) in THF/$H_2O$ (15 mL/5 mL) at room temperature was added lithium hydroxide monohydrate (0.53 g, 12.6 mmol). The resulting solution was stirred at room temperature for 2 h, quenched with 1N aqueous HCl and extracted with EtOAc. The organic layer was washed with brine, dried over $Na_2SO_4$ and concentrated in vacuo to afford acid 117 (0.69 g, 90%) as a solid. $^1$H NMR (400 MHz, DMSO-$d_6$): δ 8.21 (1H, s), 8.14 (1H, d), 8.05 (1H, d), 7.84 (1H, t), 7.65 (1H, t), 7.58 (1H, d), 7.28 (1H, S), 7.27 (1 h, d).

Using the above procedures, but substituting the appropriate anilines and bromoesters for 79 and 110, the following compounds were obtained: (3-Trifluoromethyl-phenyl)-[5-trifluoromethyl-2-(3-trifluoromethyl-phenoxy)-phenylamino]-acetic acid 113 $^1$H NMR (CDCl$_3$, 400 MHz) δ 7.46 (s, 1H), 7.38-7.28 (m, 4H), 7.11 (m, 2H), 6.97 (s, 1H), 6.85 (d, 1H), 6.66 (d, 1H), 6.52 (s, 1H); (3,5-Bis-trifluoromethyl-phenylamino)-(3-trifluoromethyl-phenyl)-acetic acid 114, $^1$H NMR (CDCl$_3$, 400 MHz) δ 7.78 (s, 1H), 7.71 (d, 1H), 7.64 (d, 1H), 7.56-7.53 (m, 1H), 7.20 (s, 1H), 6.89 (s, 1H), 5.22 (s, 1H); (3-Trifluoromethyl-phenyl)-(4-trifluoromethyl-phenylamino)-acetic acid 115, $^1$H NMR (400 MHz, DMSO-$d_6$): δ 7.87 (1H, s), 7.79 (1H, d), 7.66 (1H, d), 7.60

(1H, t), 7.34 (2H, d), 7.10 (1H, d), 6.78 (2H, d), 5.39 (1H, d) ppm; (4-Isopropyl-2-trifluoromethyl-phenylamino)-(3-trifluoromethyl-phenyl-acetic acid 116, ¹H NMR (400 MHz, DMSO-d₆): δ 8.17 (1H, d), 8.15 (1H, s), 8.04 (1H, d), 7.79 (1H, t), 7.17 (1H, d), 7.14 (1H, s), 6.77 (1H, d), 2.77 (1H, m), 1.13 (6H, d) ppm; (4-Trifluoromethyl-phenyl)-(2-trifluoromethyl-phenylamino)-acetic acid 118, ¹H-NMR (DMSO, 400 MHz): δ 7.80-6.50 (m, 8H), 5.98 (d, 1H), 5.52 (d, 1H).

Example 8

Preparation of 2-(4-trifluoromethyl-phenoxy)-2-(3-trifluoromethyl-phenyl)-propionic acid

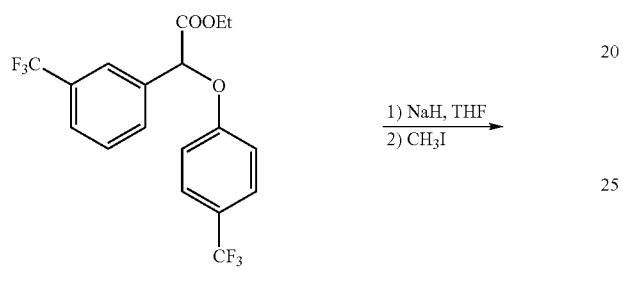

80

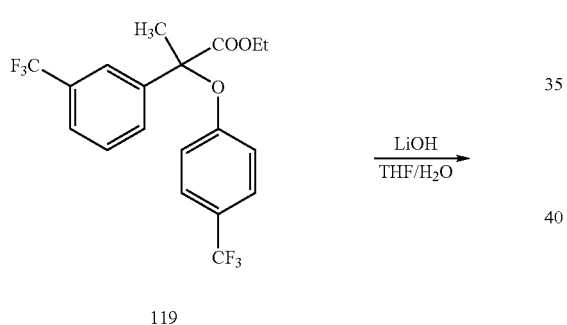

119

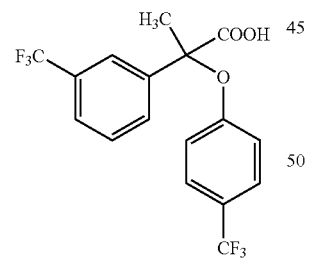

120

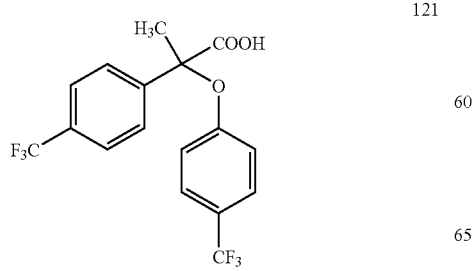

121

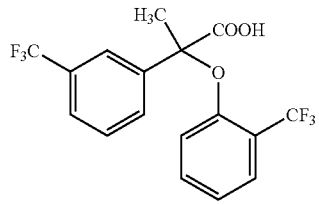

122

To a solution of ester 80 (3.01 g, 7.69 mmol) in anhyrous THF (30 mL) was added NaH (60% in oil, 0.80 g, 0.020 mol). After the resulting solution was stirred at rt for 2 h, iodomethane (2.5 mL, 0.040 mol) was added. The resulting mixture was stirred at rt overnight. The reaction was quenched with sat. NH₄Cl, diluted with EtOAc, washed with diluted aqueous HCl and brine, dried over Na₂SO₄, concentrated in vacuo, and purified by flash chromatography on silica gel (5:95 EtOAc/hexanes) to afford ester 119 (3.18 g, 87%) as a colorless liquid. ¹H NMR (400 MHz, DMSO-d₆): δ 7.91 (1H, s), 7.88 (1H, d), 7.7 (1H, d), 7.69 (1H, d), 7.65 (2H, d), 7.02 (1H, d), 4.16 (2H, q), 2.48 (3H, s), 1.03 (3H, t) ppm. To a solution of ester 119 (1.03 g, 2.17 mmol) in THF/H₂O (15 mL/5 mL) at rt was added lithium hydroxide monohydrate (0.95 g, 0.022 mol). The resulting solution was refluxed at rt for 1 h, cooled to rt, quenched with 1N aqueous HCl and extracted with EtOAc. The organic layer was washed with brine, dried over Na₂SO₄ and concentrated in vacuo to afford acid 120 (0.93 g, 96%) as a pale-yellow liquid.

Using the above procedures, but substituting the appropriate (X-phenoxy phenyl acetic esters for 80, there were obtained the following compounds: 2-(4-Trifluoromethyl-phenoxy)-2-(4-trifluoromethyl-phenyl)-propionic acid, 121; 2-(2-Trifluoromethyl-phenoxy)-2-(3-trifluoromethyl-phenyl)-propionic acid, 122, ¹H NMR (d-DMSO, 400 MHz) δ 13.85 (s, 1H), 8.04 (s, 1H), 7.86 (d, 1H), 7.74 (d, 1H), 7.70-7.66 (m, 3H), 7.56 (m, 1H), 7.15 (m, 1H), 6.89 (d, 1H), 1.89 (s, 3H).

Example 9

Preparation of (4-trifluoromethyl-phenoxy)-(3-trifluoromethyl-phenyl)-acetaldehyde, 124

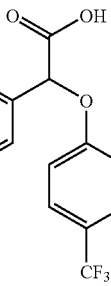

39

-continued

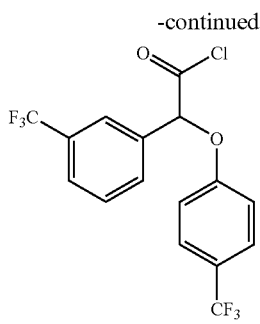

123

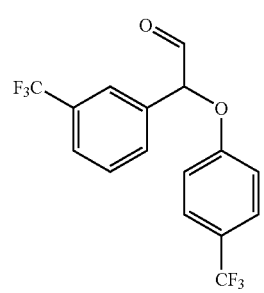

124

(4-Trifluoromethyl-phenoxy)-(3-trifluoromethyl-phenyl)-acetic acid 39 (0.05 mol) was dissolved in dichloromethane (50 mL) and thionyl chloride (5 mL) and dimethylformamide (0.1 mL) were added. After 2 hours, the solvents were removed under vacuum to afford (4-trifluoromethyl-phenoxy)-(3-trifluoromethyl-phenyl)-acetyl chloride, 123. This compound (0.01 mol) was dissolved in ether (25 mL) and the solution was cooled to −80° C. and lithium aluminum tri-tertiarybutoxy hydride (0.01 mol) was added. The progress of the reaction was monitored by TLC. When the reaction was complete, the mixture was warmed to room temperature and water was added. The organic phase was dried and concentrated and the residue was chromatographed to afford the title compound 124.

Example 10

Preparation of 2-(4-trifluoromethyl-phenoxy)-2-(3-trifluoromethyl-phenyl)-ethanol, 125

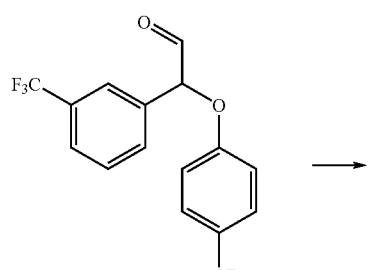

124

-continued

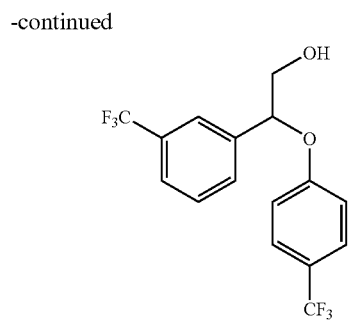

125

(4-Trifluoromethyl-phenoxy)-(3-trifluoromethyl-phenyl)-acetaldehyde, 124 (0.02 mol) was dissolved in isopropanol (20 mL) and sodium borohydride (0.02 mol) was added. The progress of the reaction was monitored by TLC. When the reaction was complete, water and ether were added. The organic phase was dried and concentrated, and the residue was chromatographed to afford the title compound 125. $^1$H-NMR (DMSO, 400MHz): δ 7.75-7.24 (m, 8H), 5.59 (μs, 1H), 5.22 (m, 1H), 3.70 (m, 2H).

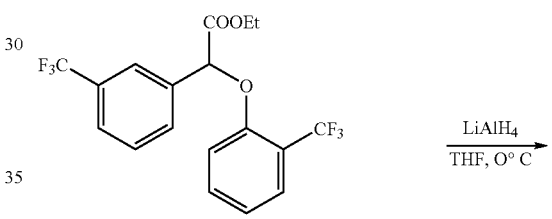

126

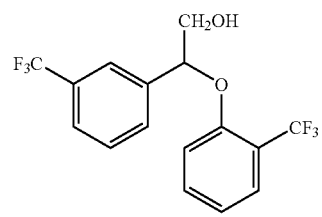

127

To a solution of ester 126 (1.04 g, 2.65 mol, prepared as described for 80) in anhyrous THF (15 mL) at 0° C. was added LiAlH$_4$ (0.10 g, 2.64 mmol). After stirring at 0° C. for 0.5 h, the reaction mixture was quenched with 15% aqueous NaOH (0.15 mL), filtered through a pad of celite, rinsed with EtOAc, concentrated in vacuo, and the residue was chromatographed on silica gel (2:8 EtOAc/hexanes) to afford 127 (0.71 g, 81%) as a colorless liquid. $^1$H NMR (400 MHz, DMSO-d$_6$): δ 7.79 (1H, s), 7.71 (1H, d), 7.65 (1H, d), 7.58-7.62 (2H, m), 7.50 (1H, t), 7.22 (1H, d), 7.03 (1H, t), 5.71 (1H, t), 5.14 (1H, t), 3.80-7.85 (1H, m), 3.77-3.72 (1H, m) ppm.

Using the above procedures, but employing different aldehydes and esters in place of 124 and 126, carbinols 128-134 were obtained.

128 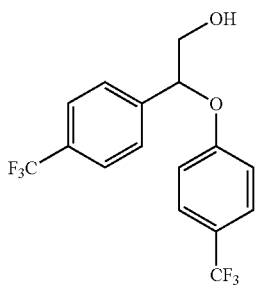

129 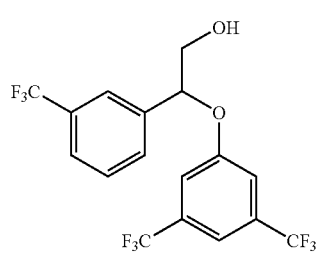

130 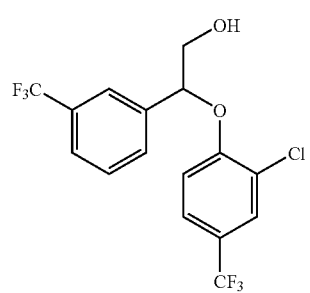

131 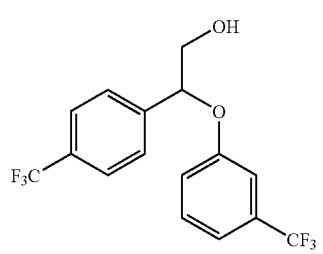

132 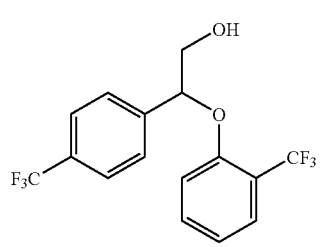

133 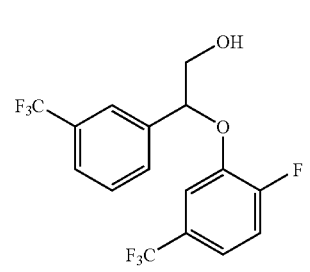

134 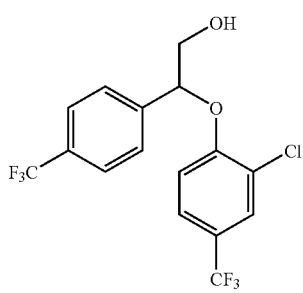

Example 11

Preparation of propionic acid 2-(4-trifluoromethyl-phenoxy)-2-(3-trifluoromethyl-phenyl)-ethyl ester, 135

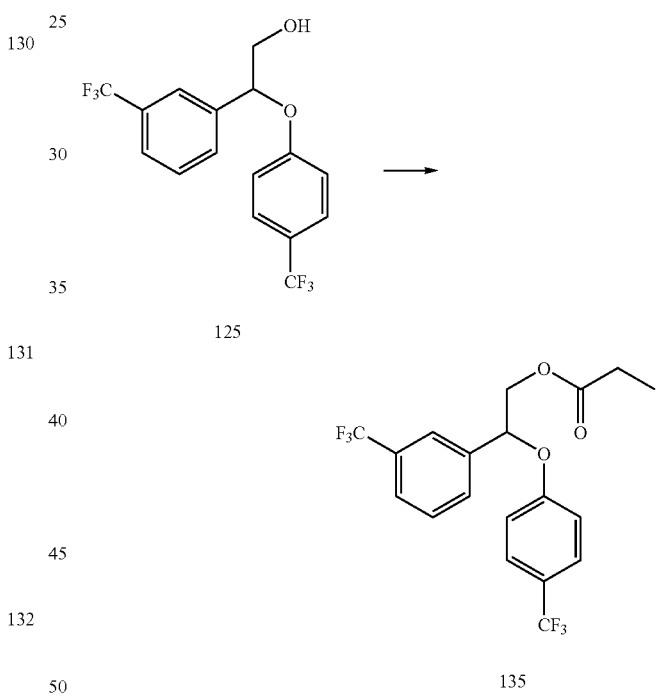

2-(4-Trifluoromethyl-phenoxy)-2-(3-trifluoromethyl-phenyl)-ethanol, 125, (0.01 mol) was dissolved in pyridine (20 mL) and the solution was cooled to 0° C. Propionyl chloride (0.015 mol) was added. The progress of the reaction was monitored by TLC. When the reaction was complete, water and ether were added. The organic phase was washed with dilute hydrochloric acid, dried and concentrated. The residue was chromatographed to afford the title compound 135.

Using the above procedure, but employing different carbinols and/or different acyl chlorides, the corresponding esters analogous to 111 can be obtained.

Example 12
Preparation of (4-trifluoromethyl-phenoxy)-(3-trifluoromethyl-phenyl)-acetic acid 2-acetylamino-ethyl ester, 136

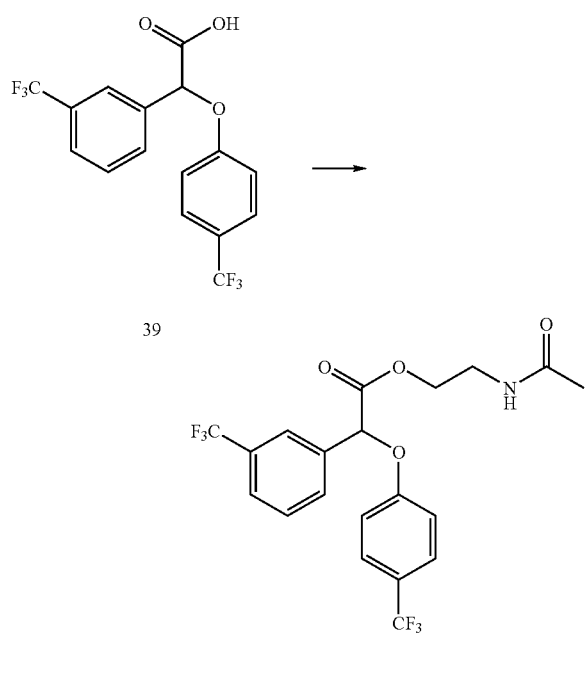

To a slurry of acid 39 (25.8 g, 0.071 mol) in anhydrous 1,2-dichloroethane (380 mL) was added thionyl chloride (16.0 mL, 0.21 mol), and then the resulting mixture was refluxed for 2 h. The mixture was cooled to rt, diluted with dry THF (150 mL) until the cloudy mixture turned clear, and then N-acetylethanolamine (39.12 g, 0.38 mol) was added. The resulting solution was stirred at rt overnight. The reaction was quenched with sat. NaHCO$_3$ carefully, diluted with EtOAc, and washed with water. The organic layer was washed with brine, dried over Na$_2$SO$_4$, concentrated in vacuo, and the residue was recrystallized from iPrOH/hexanes (11 mL/31.5 mL) to afford pure product 136 (22.78 g, 71%) as a off-white solid. $^1$H NMR (400 MHz, CDCl$_3$): δ 7.89 (1H, s), 7.80 (1H, d), 7.69 (1H, d), 7.57-7.61 (3H, t), 7.06 (2H, t), 5.78 (1H, s), 5.27 (1H, br), 4.24 (2H, m), 3.45 (2H, dd), 1.81 (3H, s) ppm.

Using the above procedure, but employing different carboxylic acids and/or different alcohols, the corresponding esters analogous to 136 are obtained.

Example 13
Preparation of (3-trifluoromethyl-phenyl)-(6-trifluoromethyl-pyridin-3-yloxy)-acetic acid 2-morpholin-4-yl-ethyl ester, 137

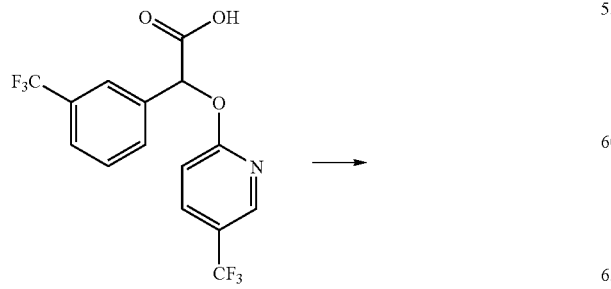

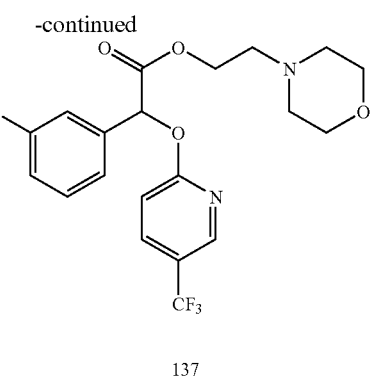

(3-Trifluoromethyl-phenyl)-(5-trifluoromethyl-pyridin-2-yloxy)-acetic acid, 100, prepared as described in Example 4, (0.05 mol) was converted into the acid chloride, using the procedure of Example 6. The acid chloride (0.01 mol) was dissolved in tetrahydrofuran (25 mL) and N,N-dimethylaniline (2 mL) and morpholinoethanol (2 mL) were added. The progress of the reaction was monitored by TLC. When the reaction was complete, water and ether were added. The organic phase was washed with dilute hydrochloric acid, dried and concentrated. The residue was chromatographed to afford the title compound 137.

Using the above procedure, but employing different carboxylic acids and/or different alcohols, the corresponding esters analogous to 137 can be obtained.

Example 14
Preparation of (5-[(4-trifluoromethyl-phenoxy)-(3-trifluoromethyl-phenyl)-methyl]-1H-tetrazole 140

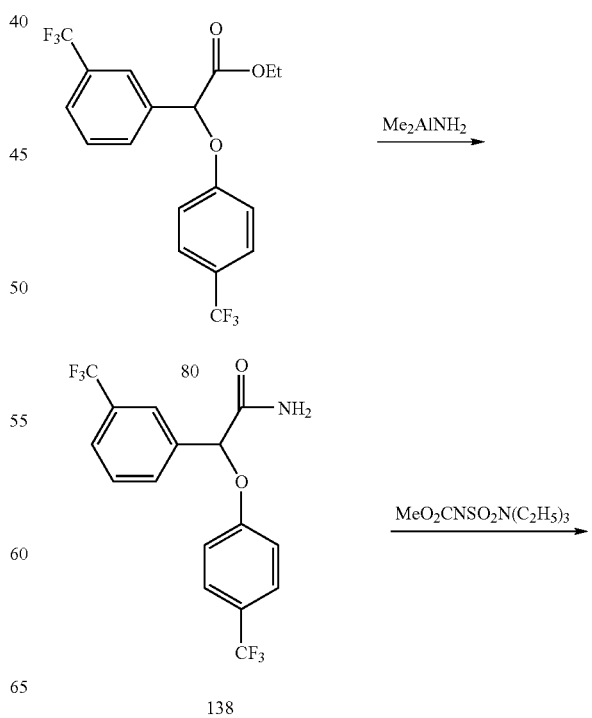

-continued

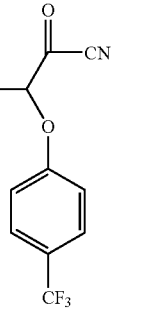

139

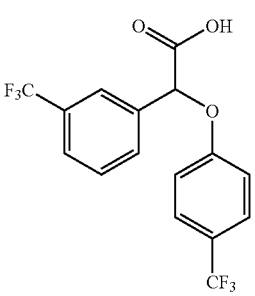

140

Dimethylaluminum amide was prepared by adding anhydrous toluene (60 mL) to ammonium chloride (2.14 g). The mixture was cooled to 0° C and trimethylaluminum in toluene (2.0 M, 20 mL) was added dropwise. The reaction was allowed to stir at 0° C. for 15 min before warming to room temperature and stirred for an additional 2 hours. To the freshly prepared dimethylaluminumamide was added the ester 80 (6.0 g) in toluene (20 mL). The reaction was then warmed to 100° C. and allowed to stir overnight. The reaction was then cooled to room temperature and $Na_2SO_4$ $10H_2O$ was added and stirred for an additional hour. Filtration followed by concentration of the solution gave a yellow liquid. Purification with flash column chromatography (hexanes/ethyl acetate 1:4) gave the amide 138 (2.7 g, 49%) as light yellow solid. $^1$H-NMR ($CDCl_3$, 400 MHz): δ 7.81-7.51 (m, 6H), 7.02 (d, 2H), 6.60 (br. 1H), 5.78 (br. 1H), 5.63 (s, 1H).

The amide 138 (2.7 g) was dissolved in dichloromethane and (methoxycarbonylsulfamoyl)triethylammonium hydroxide, inner salt (1.3 g) was then added. The resulting mixture was stirred overnight, and concentrated. Purification with flash column chromatography (hexane/ethyl acetate 5:1) gave the nitrile 139 as a white solid. $^1$H-NMR ($CDCl_3$, 400 MHz) δ 7.87-7.64 (m, 6H), 7.19 (d, 2H), 5.96 (s, 1H).

The nitrile 139 (1.05 g) was dissolved in anhydrous THF (40 mL). Trimethyltin azide (1.3 mL) was then added. The reaction mixture was refluxed overnight. The solution was then cooled to room temperature, diluted with HCl (0.5 N), and extracted with ethyl acetate. The organic solution was dried with sodium sulfate, and concentrated. Purification with flash column chromatography (ethyl acetate) gave 1.15 g of tetrazole 140 (98%) as a white solid. $^1$H-NMR ($CDCl_3$, 400 MHz): δ 7.85-7.51 (m, 6H), 7.04 (d, 2H), 6.85 (s, 1H).

Using the above procedure, but employing different carboxylic acids, the corresponding tetrazoles analogous to 140 can be obtained.

Example 15

Preparation of (4-trifluoromethyl-phenoxy)-(3-trifluoromethyl-phenyl)-acetic acid sodium salt 141

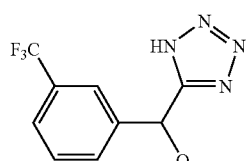

39

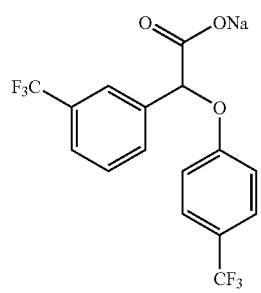

141

A solution of the acid 39 in EtOAc was treated with 1 eq. of 1N NaOH, and the resultant product was recrystallized from EtOAc/hexanes to afford white solid Na salt 141.

Using the above procedure, but employing different carboxylic acids, the corresponding salts analogous to 141 can be obtained.

Example 16

Preparation of Enantiomers of (4-trifluoromethyl-phenoxy)-(4-trifluoromethyl-phenyl)-acetic acid 83

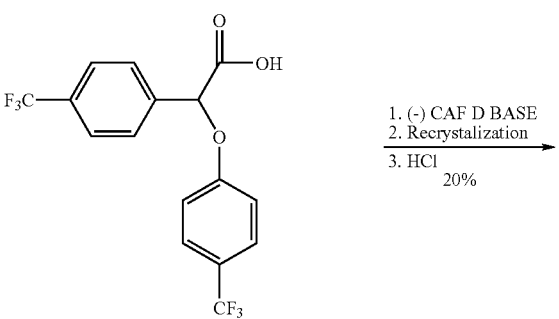

83

71

-continued

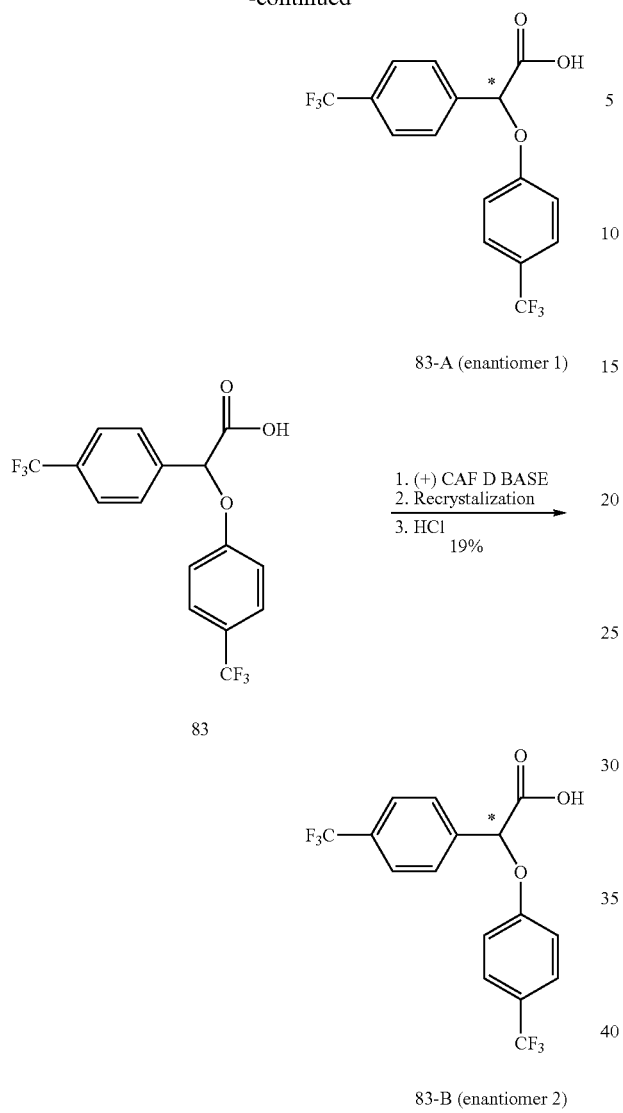

83-A (enantiomer 1)

83

A mixture of racemic acid 83 (7.97 g), and (1R,2R)-(−)-2-amino-1-(4-nitrophenyl)-1,3-propanediol (CAF D BASE) (2.56 g, 0.55 eq.) was dissolved in 70 mL of 2-propanol by heating at 75° C. for 30 min. The solution was cooled slowly to room temperature, and then was allowed to stand at 4° C. overnight. The solid (3.4 g) was collected by filtration. The solid was dissolved in 50 mL of 2-propanol at 80° C. The solution was cooled to room temperature slowly. Crystals (2.4 g) were collected by filtration. The crystals were mixed with 1 N HCl (50 mL), extracted with ethyl acetate. The organic solution was dried over $Na_2SO_4$. The solvent was removed in vacuum to give 1.6 g of enatiomerically enriched 83-A (20%) as white solid. $^1$H-NMR (DMSO, 400 MHz): δ 7.80-7.18 (m, 8H), 6.20 (s, 1H).

Using the same procedure as described above, 83-B was obtained by using (1S,2S)-(+)-2-amino-1-(4-nitrophenyl)-1,3-propanediol as the chiral base. $^1$H-NMR (DMSO, 400 MHz): δ 7.80-7.18 (m, 8H), 6.20 (s, 1H).

Using the above procedure, but employing different carboxylic acids and chiral bases, the corresponding enantiomers analogous to 83 can be obtained.

72

Example 17

Preparation of Enantiomers of (4-trifluoromethyl-phenoxy)-(3-trifluoromethyl-phenyl)-acetic acid, 39

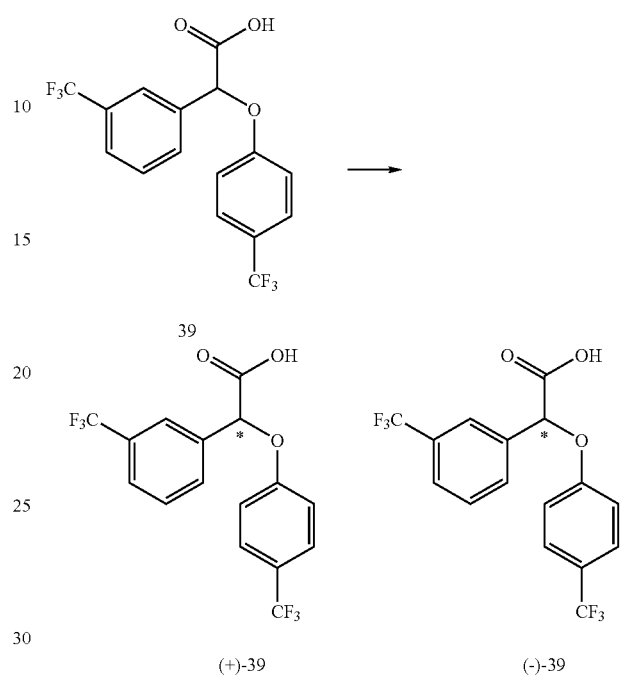

Optically pure (−)-39 salt was obtained via classical resolution by serial recrystallization of the salt of the racemic acid 39 with (1R,2R)-(−)-2-amino-1-(4-nitrophenyl)-1,3-propanediol (0.55 eq.) in EtOAc/hexanes at 75° C. to rt. The first crystal collected afforded (−)-39 salt. Serial recrystallization of the remaining mother liquid afforded another optically pure (+)-39 salt. After acidification of both salts with 1N HCl in EtOAc, optically pure (−)-39 and (+)-39 were obtained as white solids respectively. (+)-39, $[α]^{25}λ=+74.6$ (c=0.55, $CH_3OH$), and (−)-39 $[α]^{25}λ=−74.8$ (c=0.89, $CH_3OH$). Chiral HPLC analysis of enantiomers was carried out at λ=220 nm by injecting 10 μL of an approximately a 0.5 mg/mL solution of the sample dissolved in mobile phase onto a 25 cm×4.6 mm Regis Technologies (R,R) Whelk-O 15 μm column with a 1.5 mL/min flow of (1.5/98.5/0.05) iPrOH/hexanes/TFA. Under these conditions, (+)-enantiomer eluted at 6.6 min, (−) enantiomer at 8.8 min (approximate retention times).

Example 18
Separation of Enantiomers of (4-trifluoromethyl-phenoxy)-(3-trifluoromethyl-phenyl)-acetic acid, 39 by chiral HPLC

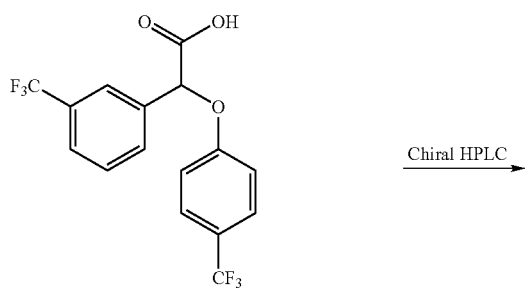

Chiral HPLC ⟶

39

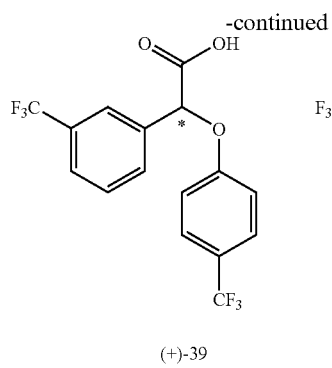
(+)-39

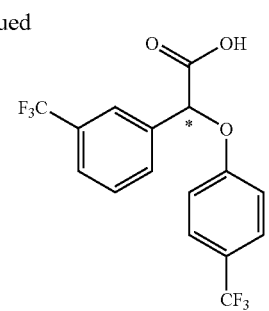
(−)-39

Racemic 39 was resolved into the enantiomers using chiral HPLC. A 25 cm×2.1 mm Regis Technologies (R,R) WHELK-O 2 10/100 column was employed at room temperature. Injection samples contained 5.0 mL of 12 mg/mL of racemic 39 in isopropanol:hexane, 2:3. The column was eluted with isopropanol:hexanes:trifluoroacetic acid 2:98:0.1, with detection at 220 nm. The separately eluted enantiomers were collected and the fractions were concentrated to afford the individual enantiomers (+)-39 and (−)-39.

The above procedure can be applied to other racemic acids of the present invention to provide their separated enantiomers.

Example 19

Preparation of Esterified Compounds

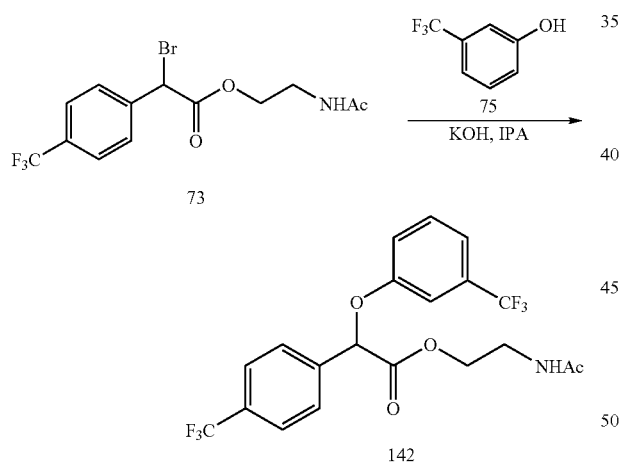

Potassium hydroxide (2.6 g, 0.046 mole) was dissolved in isopropanol (40 mL) under argon by heating to 50-60° C. The solution was the cooled to 0-10° C. in an ice bath. To this was added 3-trifluromethylphenol (6.5 mL (8.7 g), 0.053 mole), which raised the internal temperature to 10-20° C. (2-Acetamidoethyl)-4-trifluoromethylphenylbromoacetate 73 (16.2 g, 0.044 mole) was dissolved in 12 mL isopropanol and cooled to 0-10° C. The phenoxide solution was then added to the bromoester, which raised the internal temperature to 5-15° C. The resulting mixture was stirred for 4 h in the cold bath. Citric acid (1.6 g, 0.0084 mole) was added in 12 mL water. The mixture was filtered to remove white potassium bromide and the cake washed with isopropanol (20 mL). The isopropanol was rotary evaporated and the residue dissolved in ethyl acetate (72 mL) and extracted with water (24 mL). The ethyl acetate phase was dried over sodium sulfate and filtered and the filter cake washed with ethyl acetate. After rotary evaporation, crude product were obtained. This was dissolved in ethyl ether: hexane (1:1) and diluted with hexane, whereupon some material oiled out. The mixture was cooled in an Ice bath to 2-5° C. a white solid formed at once and was filtered and washed with ethyl ether: hexane (1:1) to afford 142, after drying under vacuum.

Using the above procedures, but substituting the appropriate phenols and bromoesters for 73, the following compounds were obtained: 143-147.

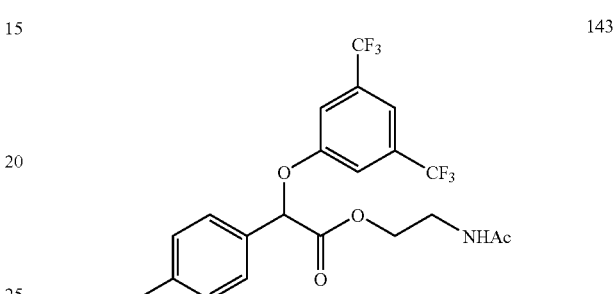
143

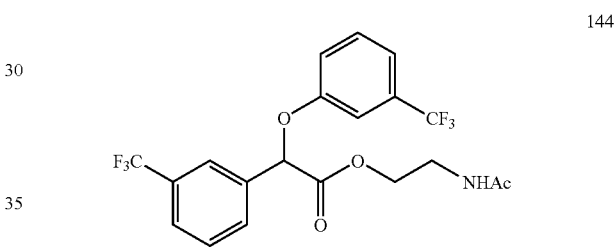
144

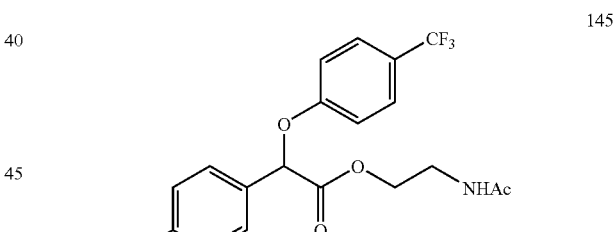
145

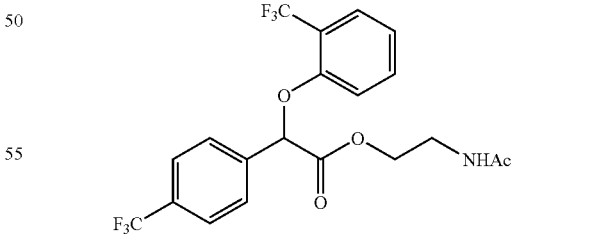
146

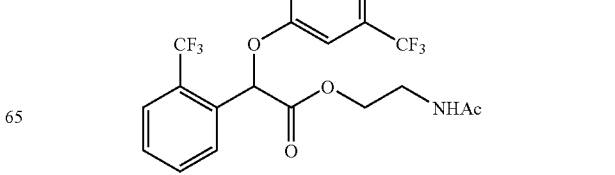
147

Example 20

In vivo Activities

The anti-diabetic activities of the compounds were evaluated in the C57BL/6j ob/ob Mice model.

A. Materials and Methods

Male, 7-9 weeks old, C57BL/6J ob/ob mice were purchased from The Jackson Laboratory (Bar Harbor, Me., USA). Animals were housed (4-5 mice/cage) under standard laboratory conditions at 22±3° C. temperature and 50±20% relative humidity, and were maintained on a diet of Purina rodent chow and water ad libitum. Prior to treatment, blood was collected from the tail vein of each animal. Mice that had non-fasting plasma glucose levels between 250 and 500 mg/dl were used. Each treatment group consisted of 8-10 mice that were distributed so that the mean glucose levels were equivalent in each group at the start of the study. Mice were dosed orally by gavage once a day for 1-4 days with vehicle and one or more dose of test compound at a dose ranging from 5 to 125 mg/kg. Compounds were delivered in a liquid formulation containing 5% (v/v) dimethyl sulfoxide (DMSO), 1% (v/v) Tween 80® and 0.9% (w/v) methylcellulose. The gavage volume was 10 ml/kg. Blood samples were taken at 6 hours after the each dose and analyzed for plasma glucose. Food intake and body weight were measured daily. Plasma glucose concentrations were determined calorimetrically using a commercial glucose oxidase method (Sigma Chemical Co, St. Louis, Mo., USA). Significant difference between groups (comparing drug-treated to vehicle-treated) was evaluated using the Student unpaired t-test.

B. Results

Table 1 provides the relative potency of some selected compounds of the invention. Compounds that are effective for glucose lowering at the dose of ≦125 mg/kg are assigned a potency of ++; compounds that are less effective for glucose lowering, typically exhibiting activity at a multiple dose or elevated dose of >125 mg/kg is assigned the potency of +.

TABLE 1

Potency of Invention Compounds

| Number | Compound # | Potency | Insulin Level compared with vehicle |
|---|---|---|---|
| 1 | 39 | ++ | Lower |
| 2 | 81 | ++ | Lower |
| 3 | 83 | ++ | Lower |
| 4 | 85 | ++ | Lower |
| 5 | 86 | ++ | Lower |
| 6 | 89 | ++ | Lower |
| 7 | 100 | ++ | Lower |
| 8 | 120 | ++ | Lower |
| 9 | 121 | ++ | Lower |
| 10 | 128 | ++ | Lower |
| 11 | 136 | ++ | Lower |
| 12 | (−)-39 | ++ | Lower |
| 13 | (+)-39 | ++ | Lower |
| 14 | 142 | ++ | Lower |
| 15 | 143 | ++ | Lower |
| 16 | 144 | ++ | Lower |
| 17 | 145 | ++ | Lower |
| 18 | 146 | + | Lower |
| 19 | 147 | + | Lower |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula

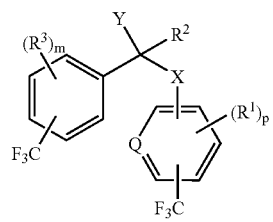

and all pharmaceutically acceptable salts and prodrugs thereof, wherein

X is a member selected from the group consisting of O, and NR, wherein R is H,

Y is a member selected from the group consisting of $CH_2OR^c$ and $CO_2R^c$, wherein $R^c$ is a member selected from the group consisting of H, $(C_1-C_8)$alkyl, and $(C_1-C_8)$alkylene-Z, wherein Z is selected from the group consisting of $COR^d$, $COOR^d$, $NR^dR^e$, $NR^dCON-R^eR^f$, $NR^dCOR^e$, $NR^dCOOR^e$ and $CONR^dR^e$ wherein $R^d$, $R^e$ and $R^f$ are each independently selected from the group consisting of H, $(C_1-C_8)$alkyl and phenyl;

each $R^1$ and $R^3$ is a member independently selected from the group consisting of halogen, $(C^1-C^8)$alkyl, $(C_1-C_8)$ alkoxy, $(C_1-C_8)$haloalkyl, $O(C_1-C^8)$haloalkyl, and nitro;

$R^2$ is a member selected from the group consisting of H and $CH_3$;

Q is C the subscript m is an integer of from 0 to 2; and the subscript p is an integer of from 0 to 1.

2. A compound of claim 1, wherein Y is $CO_2R^c$.

3. A compound of claim 1, wherein each $R^1$ is selected from the group consisting of halogen, nitro, $(C_1-C_8)$ alkyl and $(C_1-C_8)$ alkoxy; and each $R^3$ is selected from the group consisting of halogen, nitro, $(C_1-C_8)$ alkyl and $(C_1-C_8)$ alkoxy.

4. A compound of claim 3, wherein X is O and Y is $CO_2R^c$.

5. A compound of claim 3, wherein X is O and Y is $CH_2OR^c$.

6. A compound of claim 3, wherein X is NH and Y is $CO_2R^c$.

7. A compound of claim 3, wherein X is NH and Y is $CH_2OR^c$.

8. A composition comprising a pharmaceutically acceptable excipient and a compound having a formula:

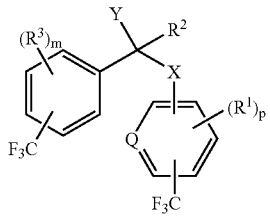

and all pharmaceutically acceptable salts and prodrugs thereof, wherein
- X is a member selected from the group consisting of O, and NR, wherein R is H,
- Y is a member selected from the group consisting of $CH_2OR^c$ and $CO_2R^c$, wherein $R^c$ is a member selected from the group consisting of H, $(C_1-C_8)$alkyl, and $(C_1-C_8)$alkylene-Z, wherein Z is selected from the group consisting of $COR^d$, $COOR^d$, $NR^dR^e$, $NR^dCON-R^eR^f$, $NR^dCOR^e$, $NR^dCOOR^e$ and $CONR^dR^e$ wherein $R^d$, $R^e$ and $R^f$ are each independently selected from the group consisting of H, $(C_1-C_8)$alkyl and phenyl;
- each $R^1$ and $R^3$ is a member independently selected from the group consisting of halogen, $(C_1-C_8)$alkyl, $(C_1-C_8)$alkoxy, $(C_1-C_8)$haloalkyl, $O(C_1-C_8)$haloalkyl, and nitro,
- $R^2$ is a member selected from the group consisting of H and $CH_3$;
- Q is C
- the subscript m is an integer of from 0 to 2; and
- the subscript p is an integer of from 0 to 1.

9. A compound selected from the group consisting of:
(4-Trifluoromethyl-phenoxy)-(3-trifluoromethyl-phenyl)-acetic acid;
(2-Trifluoromethyl-phenoxy)-(3-trifluoromethyl-phenyl)-acetic acid;
(4-Trifluoromethyl-phenoxy)-(4-trifluoromethyl-phenyl)-acetic acid;
(3,5-Bis-trifluoromethyl-phenoxy)-(3-trifluoromethyl-phenyl)-acetic acid;
(2-Chloro-4-trifluoromethyl-phenoxy)-(3-trifluoromethyl-phenyl)-acetic acid;
(3-Trifluoromethyl-phenoxy)-(4-trifluoromethyl-phenyl)-acetic acid;
(2-Trifluoromethyl-phenoxy)-(4-trifluoromethyl-phenyl)-acetic acid;
(2-Chloro-4-trifluoromethyl-phenoxy)-(4-trifluoromethyl-phenyl)-acetic acid;
(2-Fluoro-5-trifluoromethyl-phenoxy)-(4-trifluoromethyl-phenyl)-acetic acid;
(3-Fluoro-5-trifluoromethyl-phenyl)-(5-methoxy-2-trifluoromethyl-phenoxy)-acetic acid;
(2,4-Bis-trifluoromethyl-phenoxy)-(3-trifluoromethyl-phenyl)-acetic acid ethyl ester;
(3-Trifluoromethyl-phenyl)-(2-trifluoromethyl-phenylamino)-acetic acid;
(3-Trifluoromethyl-phenyl)-(3-trifluoromethyl-phenylamino)-acetic acid;
(3,5-Bis-trifluoromethyl-phenylamino)-(3-trifluoromethyl-phenyl)-acetic acid;
(3-Trifluoromethyl-phenyl)-(4-trifluoromethyl-phenylamino)-acetic acid;
(4-Isopropyl-2-trifluoromethyl-phenylamino)-(3-trifluoromethyl-phenyl)-acetic acid;
(4-Trifluoromethyl-phenyl)-(2-trifluoromethyl-phenylamino)-acetic acid;
2-(4-Trifluoromethyl-phenoxy)-2-(3-trifluoromethyl-phenyl)-propionic acid;
2-(4-Trifluoromethyl-phenoxy)-2-(4-trifluoromethyl-phenyl)-propionic acid;
2-(2-Trifluoromethyl-phenoxy)-2-(3-trifluoromethyl-phenyl)-propionic acid;
2-(4-trifluoromethyl-phenoxy)-2-(3-trifluoromethyl-phenyl)-ethanol;
(4-trifluoromethyl-phenoxy)-(3-trifluoromethyl-phenyl)-acetic acid 2-acetylamino-ethyl ester;
(4-trifluoromethyl-phenoxy)-(3-trifluoromethyl-phenyl)-acetic acid sodium salt;
(+)-(4-trifluoromethyl-phenoxy)-(3-trifluoromethyl-phenyl)-acetic acid; and
(−)-(4-trifluoromethyl-phenoxy)-(3-trifluoromethyl-phenyl)-acetic acid.

10. A compound selected from the group consisting of:

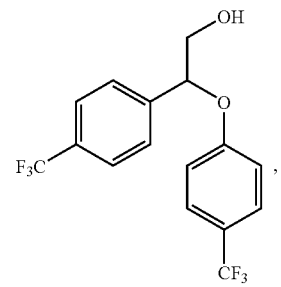

,

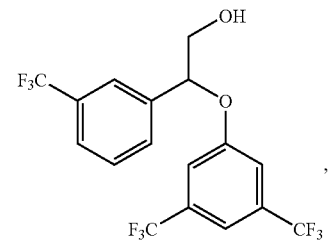

,

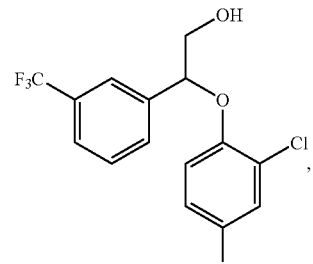

,

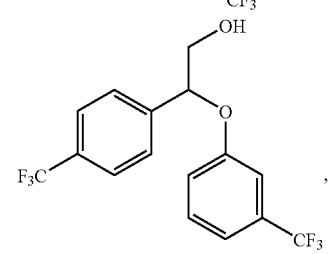

,

-continued
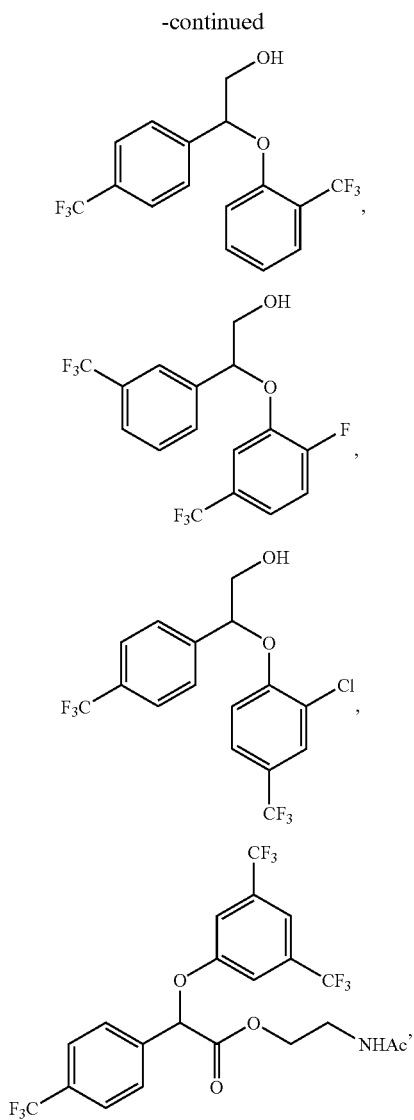
-continued
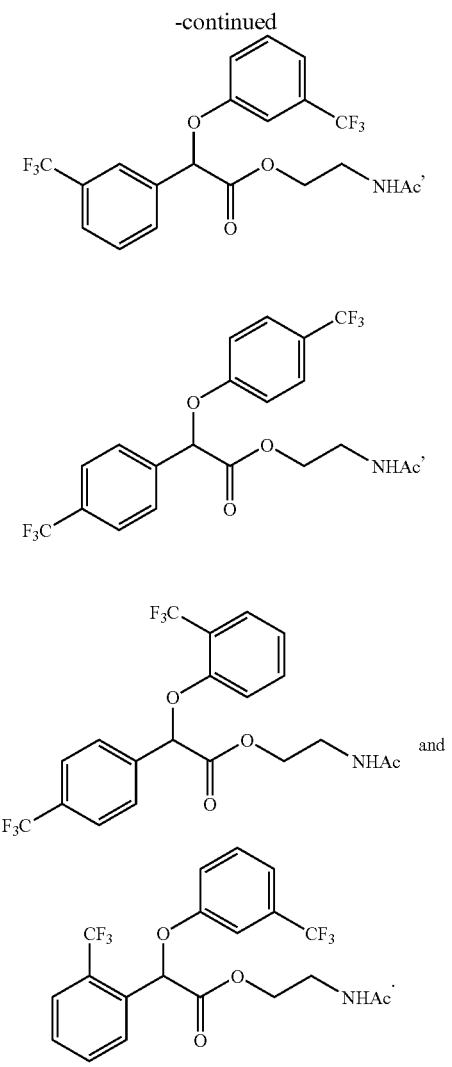
* * * * *